United States Patent [19]

Scribner

[11] 4,032,533
[45] June 28, 1977

[54] 3,4-DISUBSTITUTED-1,3,4-THIADIAZO-LINE-2,5-DIONES

[75] Inventor: Richard Merrill Scribner, Wilmington, Del.

[73] Assignee: E. I. Du Pont de Nemours and Company, Wilmington, Del.

[22] Filed: Feb. 19, 1976

[21] Appl. No.: 659,511

[52] U.S. Cl. .................. 260/302 D; 260/476 R; 260/486 H; 260/515 A; 260/593 H; 260/596; 260/638 R; 424/270

[51] Int. Cl.$^2$ .................................... C07D 285/10

[58] Field of Search ............... 260/302 D; 424/270

[56] References Cited

UNITED STATES PATENTS 3,558,661  1/1971  Zumach et al. ............... 260/302 D

*Primary Examiner*—R. Gallagher
*Attorney, Agent, or Firm*—Anthony P. Mentis

[57] ABSTRACT

Selected 3,4-disubstituted-1,3,4-thiadiazoline-2,5-diones are prostaglandin mimics or antagonists, and have uses typical of such compounds, such as inhibitors of gastric secretion, labor inducers, bronchodilators, topical antiinflammatory agents, etc.

16 Claims, No Drawings

3,4-DISUBSTITUTED-1,3,4-THIADIAZOLINE-2,5-DIONES

BACKGROUND OF THE INVENTION

1. Field of the invention

This invention relates to 3,4-disubstituted-1,3,4-thiadiazoline-2,5-diones having two different aliphatic substituents on the nuclear nitrogen atoms. The 3-substituent is an aliphatic omega-carboxylate such as an alkanoate, alkenoate, alkynoate, or methylenebenzenealkanoate, and the 4-substituent is a hydroxy-substituted aliphatic group. The compounds are obtained by selective alkylation of the nitrogen atoms of 1,3,4-thiadiazoline-2,5-dione, and their biological properties resemble those of the prostaglandins and their derivatives.

2. Prior Art

3-Pyrazolidinones and pyrazolidines with biological activities resembling those of prostaglandins form the subject of U.S. Pat. 3,873,566. K. Rufenacht, *Helv. Chim. Acta*, 51, 518 (1968) has described the preparation of 4-hydroxymethyl- and 4-chloromethyl-2-methoxy-1,3,4-thiadiazol-5-ones and several of their derived dithiophosphoric acid esters as insecticides and acaricides by a different procedure from the present invention. S. W. Moje, Ph.D. thesis, University of Illinois, 1974, and S. W. Moje and P. Beak, *J. Org. Chem.*, 39, 2951 (1974), disclose that both the mono- and di-potassium salts of 1,3,4-thiadiazoline-2,5-dione in DMF at 25°, on treatment with alkyl halides (benzyl bromide, methyl iodide, allyl bromide, and tert-butyl bromide) gave only the symmetrical dialkylated products. G. Ambrus et al, *Prostaglandins*, 10, No. 4, 661 (1975) disclose certain thiazole derivatives of prostaglandins. None of the references suggest the 3,4-disubstituted-1,3,4-thiadiazoline-2,5-diones of this invention.

SUMMARY OF THE INVENTION

The invention is a compound having the general formula

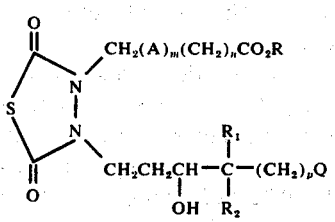

wherein
A is CH=CH, C ≡ C, or $C_6H_4$ (i.e. phenylene);
R is H, alkali metal, alkyl or cycloalkyl of up to 10 carbons, $NHC(CH_2OH)_3$ or $NR_3R_4R_5R_6$ wherein $R_3$ is H,
$R_4$, $R_5$ and $R_6$ individually are H, alkyl of 1-4 carbons or hydroxyalkyl of 2-4 carbons with the proviso that the total number of carbon atoms in $R_4$, $R_5$ and $R_6$ does not exceed 10;
$m$ is 0 or 1;
$n$ is 2 to 6;
$p$ is 0 to 6;
$R_1$ and $R_2$ individually are H, F or $CH_3$; and
Q is H, $CH_3$, $CF_2CH_3$ or $CF_3$.

The preferred compounds of the invention are those in which
A is CH=CH, C ≡ C, or p-$C_{64}$;

when $m$ is 0, $n$=5;
when $m$ is 1, $n$=2 or 3;
R is H, Na, $(CH_3)_3NH$, $(HOCH_2)_3CNH_3$, $CH_3$, $C_2H_5$, $(CH_3)_3C$, n-$C_{10}H_{21}$, or n-$C_{12}H_{25}$;
$R_1$ and $R_2$ are each H, F, or $CH_3$;
$p$ is 3 or 4; and
Q is H, $CH_3$, or $CF_3$.

When A is CH=CH or C ≡ C the preferred chain length of the —$CH_2(A)_m(CH_2)_nCO_2$— chain is 7 carbon atoms.

The invention also relates to compositions containing these compounds as prostaglandin mimics and antagonists, and as topical antiinflammatory agents.

DETAILS OF THE INVENTION

The compounds are obtained by the following reaction scheme.

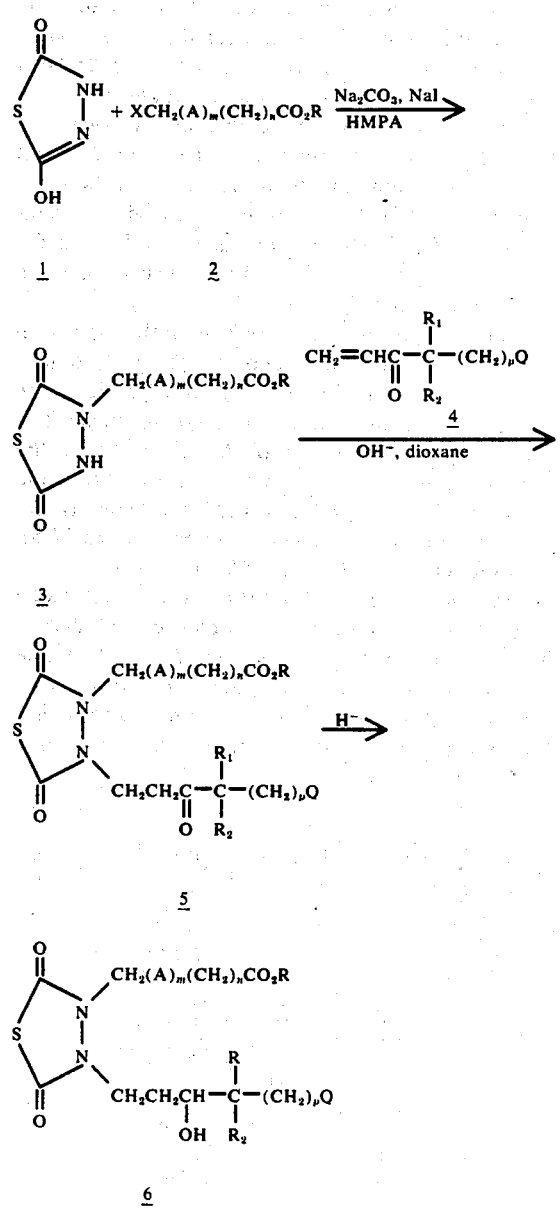

Reaction of equimolar amounts of 1,3,4-thiadiazoline-2,5-dione (1) and an omega-halocarboxylate (2) in hexamethylphosphoric triamide (HMPA) solvent in the presence of 1 to 2 molar equivalents of sodium bicarbonate produces the 3-substituted-1,3,4-thiadiazoline-2,5-dione (3). The omega-halocarboxylate (2) can be an omega-haloalkanoic acid ester, an omega-haloalkenoic acid ester, an omega-haloalkynoic acid ester, or an omega-halo(methylenebenzene)alkanoic acid ester, wherein X is chlorine, or preferentially bromine or iodine. When X is Cl or Br it is advantageous to carry out the reaction in the presence of 0.02 to 1.0 molar equivalent of sodium iodide. The reaction temperature is preferentially 25° C for a period of 4 to 5 days, although reaction temperature up to 100° C can be employed with shorter reaction times.

The 4-position of the resulting 2,5-dioxo-1,3,4-thiadiazoline-3-alkanoic acid esters, 2,5-dioxo-1,3,4-thiadiazoline-3alkenoic acid esters, 2,5-dioxo-1,3,4-thiadiazoline -esters, and 2,5-dioxo-1,3,4-thiadiazoline-3-methylenebenzenealkanoic acid esters can then be alkylated with 1.25-1.5 molar equivalents of a vinyl ketone (4) in dioxane solvent, in the presence of a trace of base such as benzyltrimethylammonium hydroxide, to produce the 3,4-dialkylated ketone (5). The reaction temperature can be between 25° and 101°, the reflux temperature of dioxane, and the reaction times can be from 2 to 24 hr. The preferred temperature is that of refluxing dioxane (101°), and the preferred reaction time is 2 to 4 hr, to ensure complete conversion of 3 to 5.

The carbonyl group of the sidechain in the 4-position of 5 can be reduced to a secondary hydroxyl group as in structue 6, using sodium or zinc borohydride as the reducing agent in dioxane and ethanol mixtures. The ethanol and borohydride can be added directly to the dioxane solution of the ketone 5 without isolation and purification of 5. The preferred reduction temperature is 25° C, and the preferred reaction time is 18 to 24 hr. to ensure complete reduction of 5 to 6.

The starting material, 1,3,4-thiadiazoline-2,5-dione (1) is prepared by demethylation of structure 7 (infra) with anhydrous HBr in glacial acetic acid (cf. Example 1). Structure 7 is formed from phosgene and the reaction product of potassium methyl xanthate and hydrazine by the procedure of K. Rufenacht, Helv. Chim. Acta, 51, 518 (1968).

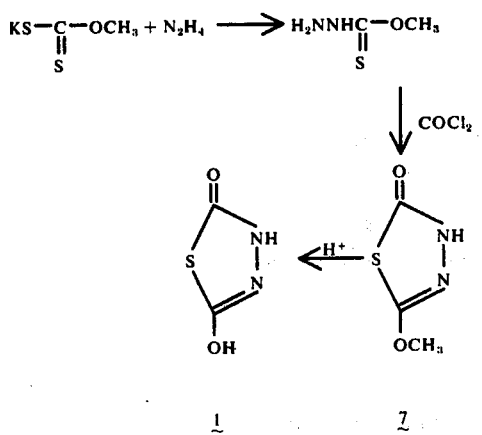

Structure 1 can exist in the three tautomeric forms 1a, 1b, and 1c:

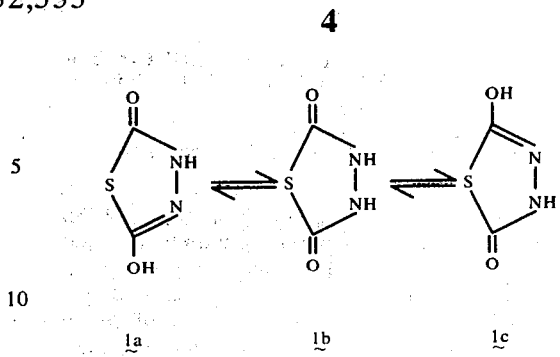

Because of this the molecule acts as if it were symmetrical, i.e., both nitrogen atoms are chemically equivalent, and no positional isomers can be expected from the transformations 1 → 3 → 5. On account of the ready inversion of trivalent nitrogen, no new centers of asymmetry are introduced during the alkylation of the 3- and 4-position and the stereochemistry of the intermediate ketone is determined by that of the sidechains. The reduction of the ketonic carbonyl group of the 4-substituent in 5 with sodium borohydride produces both stereoisomers of alcohol 6; this enantiomeric mixture need not be resolved into the individual d- and l-forms.

The carboxylic acid esters 6 may be converted to the corresponding acids, e.g., 8 (as in Example 3)

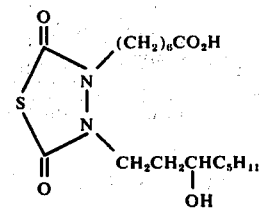

by acid treatment. The tert-butyl ester is preferred for this conversion.

The compounds of the invention are preferably named with 1,3,4-thiadiazoline-2,5-dione as the important feature, but the compound of Example 1, for instance, can also be named as a prostanoic acid derivative, e.g., dl-15-hydroxy-9,11-diketo-10-thia-8,12-diazaprostanoic acid ethyl ester; or as a prostaglandin, e.g., 15-(R,S)-tetrahydro-10-thia-8,12-diazaprostaglandin $A_1$.

EMBODIMENTS OF THE INVENTION

The following illustrative examples demonstrate ways of carrying out the invention. All parts and percentages are by weight, and all temperatures are in degrees Centigrade unless otherwise stated. The compounds are generally prepared as racemic forms.

EXAMPLE 1

4-(3-Hydroxyoctyl)-2,5-dioxo-1,3,4-thiadiazoline-3-heptanoic acid, Ethyl Ester (6)

$m = 0, n = 5, p = 4, Q = CH_3, R = C_2H_5,$
$R_1 = R_2 = H$

A. 1,3,4-Thiadiazoline-2,5-dione (1)

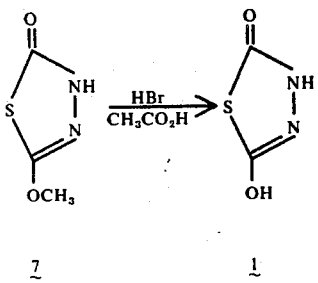

2-Methoxy-1,3,4-thiadiazol-5(4H)-one (7) was prepared from phosgene, potassium methyl xanthate, and hydrazine according to the method of K. Rufenacht, *Helv. Chim. Acta*, 51, 518 (1968). This was hydrolyzed to 1 by the following procedure. A mixture of 50 g of thiadiazole 7 in 300 ml of acetic acid was warmed to 80° to effect solution and then cooled to 70°, whereupon HBr gas was bubbled rapidly into the solution for 25 min. The HBr was shut off, the mixture was held at 70° for 35 min, and then it was cooled to 10°. Ether (200 ml) was added and the mixture was cooled back to 10°. The mixture was filtered through sintered glass and the filter cake was washed with ether, giving 37 g (75%) of 1,3,4-thiadiazoline-2,5-dione or 2-hydroxy-1,3,4-thiadiazol-5-(4H)-one (1). A thirty-gram sample was crystallized from 300 ml of ethanol, affording 18 g of pure 2, mp 175°–255°, infrared maxima (IR), $\nu_{max}$ 1700 and 1680 cm$^{-1}$, ultraviolet maxima (UV), $\lambda_{max}$ (EtOH) 235 nm ($\epsilon$ 3000) and $\lambda_{max}$ (EtOH + NaOH), 258 nm ($\epsilon$ 2330), high resolution mass spectrum (HRMS), m/e calculated for $C_2H_2N_2O_2S$ (M$^+$): 117.9837; measured: 117.9825.

Anal. Calcd for $C_2H_2N_2O_2S$: C, 20.3; H, 1.70; N, 23.8; S, 27.1. Found: C, 20.22; H, 1.62; N, 23.92; 20.02; H, 1.71; N, 23.78; S, 26.79.

B. 2,5-Dioxo-1,3,4-thiadiazoline-3-heptanoic acid, Ethyl Ester (3) $m = 0$, $n = 5$, $R = C_2H_5$

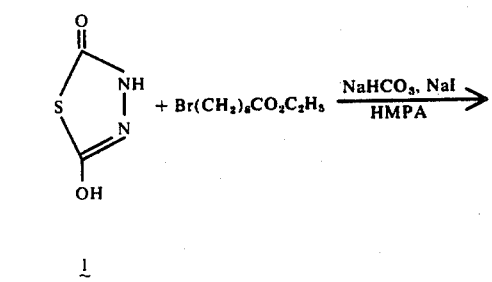

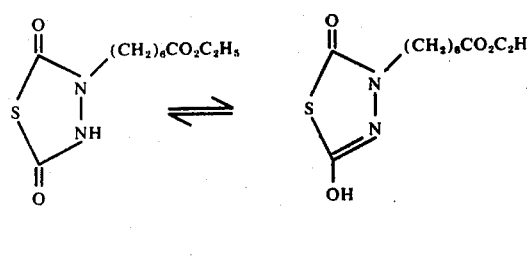

A mixture of 7.1 g (60 mmole) of 1,3,4-thiadiazoline-2,5-dione (1), 14.2 g (60 mmole) of ethyl 7-bromoheptanoate, 10 g of sodium bicarbonate, 0.3 g of sodium iodide and 50 ml of hexamethylphosphoric triamide (HMPA) was stirred at room temperature for 4 days. The reaction mixture was poured in 500 ml of 2.5% aq. HCl and extracted twice with ether; the ether extract was washed successively with water and satd. NaCl, dried over Na$_2$SO$_4$, and evaporated, giving 12.5 g of colorless oil. This oil was partitioned between 200 ml of 3% aq. NaHCO$_3$ and ether. The aqueous layer was washed with fresh ether, and the ether layers were discarded. The aqueous layer was acidified with aq. HCl and extracted twice with ether. Evaporation of the dried ether extract gave 3.8 g (13.9 mmole, 23%) of 2,5-dioxo-1,3,4-thiadiazoline-3-heptanoic acid, ethyl ester, IR, $\nu_{max}$ 3100 (NH,OH), 2800–2600 (H-bonded OH), 1730 (CO$_2$C$_2$H$_5$), and 1680–1650 cm$^{-1}$ (amide), proton magnetic resonance spectrum (pmr), (CDCl$_3$, TMSi) $\delta$ 9.45 (s, 1H, OH,NH), 4.13 (q, 2H,OCH$_2$), 3.75 (t,2H,NCH$_2$), and 1.25 ppm (t, 3H, CH$_3$), HRMS, m/e calculated for $C_{11}H_{18}N_2O_4S$ (M$^+$): 247.0986; measured: 274.0985.

Similarly 5.9 g of 1 on treatment with 14.2 g of ethyl 7-iodoheptanoate in 50 ml of HMPA gave 3.16 g of 2,5-dioxo-1,3,4-thiadiazoline-3-heptanoic acid ethyl ester with UV $\lambda_{max}$ 255 nm ($\epsilon$ 3541) and 240 (2960). From the ether phase resulting from partitioning of total crude product between ether and 5% NaHCO$_3$ there was isolated 7.2 g of N,N'dialkylated product, identified by its neutral behavior (cf. dialkylated compounds described by S. W. Moje and P. Beak, 39, 2951 (1974)) and UV $\lambda_{max}$(EtOH) 238 nm ($\epsilon$ 3880) and 233 (5500).

C. 4-(3-Hydroxyoctyl)-2,5-dioxo-1,3,4-thiadiazoline-3-heptanoic acid, Ethyl Ester (6) $m = 0$, $n = 5$, $p = 4$, $Q = CH_3$, $R = C_2H_5$, $R_1 = H$

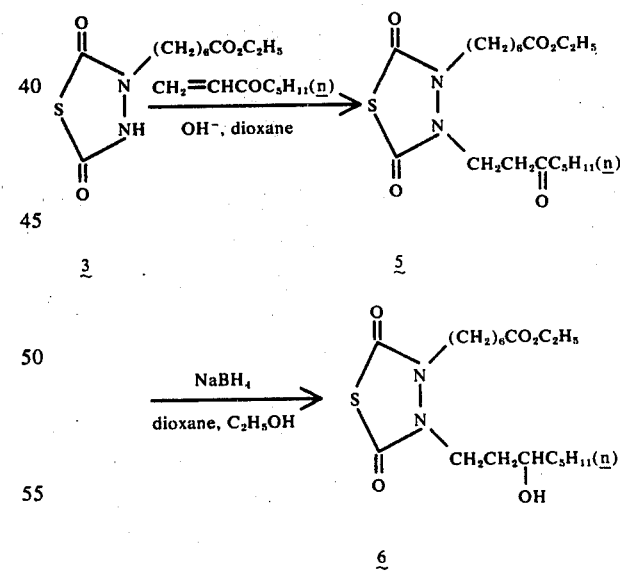

Amyl vinyl carbinol (b.p. 47°/15 mm) can be prepared by reaction by amylmagnesium bromide with acrolein. The carbinol can be oxidized to amyl vinyl ketone conviently by the aqueous chromic acid/ether oxidation method of H. C. Brown (*J. Org. Chem.* 36, 387 (1971)); and 25 percent excess of oxidant is employed and the reaction is carried out at 5°–10°. The ketone is fractionally distilled through a spinning band column and boils at 64°/16 mm. A polymerization inhibitor, e.g., p-methoxyhydroquinone, 0.2 percent by wt. is added to the distillate to prevent polymerization during storage.

A solution of 4.23 g (15.4 mmole) of 2,5-dioxo-1,3,4-thiadiazoline-3-heptanoic acid ethyl ester, 2.86 g (23 mmole) of amyl vinyl ketone, and 1 drop of benzyltrimethylammonium hydroxide (40% in methanol) in 50 ml of dry dioxane was heated at reflux temperature for 3.5 hr. Thin layer chromatography on silica gel (1:1 $CHCl_3$-ether; $I_2$ visualization) showed that conversion to 4-(3-oxooctyl)-2,5-dioxo-1,3,4-thiadiazoline-3-heptanoic acid ethyl ester (5) was complete in 2 hr. To the cooled reaction mixture 3 drops of glacial acetic acid was added followed by 100 ml of ethanol. To the ice-bath cooled solution was then added all at once 0.5 g (13 mmole) of sodium borohydride. After 25 min the ice bath was removed, the reaction mixture was stirred for 18 hr, and then evaporated in vacuo to remove most of the ethanol. The residue was mixed with 200 ml of 5% HCl and extracted twice with ethyl acetate. The ethyl acetate was washed twice with 5% $NaHCO_3$, dried, and evaporated to give 5.8 g of an oil. Chromatography of 5.4 g of this oil on 200 ml of Silicar CC-7 silica gel gave on elution with choroform 3.7 g (60%) of 4-(3-hydroxyoctyl)-2,5-dioxo-1,3,4-thiadiazoline-3-heptanoic acid ethyl ester (6), homogeneous by TLC ($R_f$ 0.41, silica gel, 1:1 $CHCl_3$-ether, $I_2$ visualization); UV spectrum showed only end adsorption in EtOH and in EtOH with NaOH (Cf 1 in Part A above), HRMS, m/e calculated for $C_{19}H_{34}N_2SO_5(M^+)$: 402.2186; measured: 402.2165.

EXAMPLE 2

4-(3-Hydroxyoctyl)-2,5-dioxo-1,3,4-thiadiazoline-3-heptanoic acid, tert-Butyl Ester (6) $m = 0, n = 5, p = 4, Q = CH_3, R = C(CH_3)_3, R_1 = R_2 = H$ A. 2,5-Dioxo-1,3,4-thiadiazoline-3-heptanoic acid, tert-Butyl Ester (3) $m = 0, n = 5, R = C(CH_3)_3$

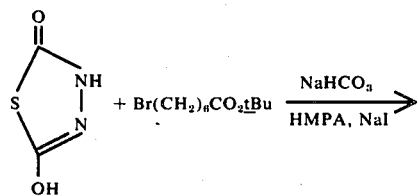

1

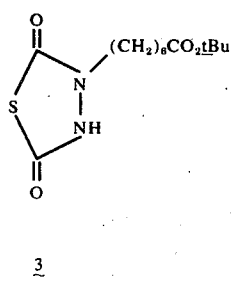

3

A solution of 11.8 g (0.1 mole) of 1,3,4-thiadiazoline-2,5-dione (1) (Example 1A) in 75 ml of HMPA was stirred with 9.24 g (0.11 mole) of $NaHCO_3$ at room temperature for 18 hrs and then 0.3 g NaI was added followed by 26.5 g (0.1 mole) of tert-butyl 7-bromoheptanoate which was added dropwise over a period of 2 hr. The reaction mixture was stirred at room temperature for 5 days then poured with stirring into 500 ml of ice-cold 5% HCl topped with 200 ml of ether. The ether phase was washed with water and then with three 100-ml portions of 2.5% $NaHCO_3$. The combined $NaHCO_3$ solutions were washed with fresh ether, topped with 200 ml of fresh ether, and while being cooled in ice, acidified by dropwise addition of conc. HCl to pH 2–3. The ether layer was drawn off, two more ether extractions of the aqueous layer were made, and the combined ether extract was washed once with satd. NaCl, dried over $Na_2SO_4$, and evaporated. 2,5-Dioxo-1,3,4-thiadiazoline-3-heptanoic acid tert-butyl ester (6.58 g, 22%) was obtained as an oil, IR, (neat) $v_{max}$ 1835 and 1725 ($CO_2$t-Bu), and 1675 $cm^{-1}$ (amide), pmr, ($CDCl_3$, TMS) δ 8.70 (s,1H,OH,NH), 3.75 (t, 2H, $NCH_2$), 2.22 (t, 2H, $CH_2CO_2$), and 1.45 ppm (s, 9H $C(CH_3)_3$).

B.

4-(3-Hydroxyoctyl)-2,5-dioxo-1,3,4-thiadiazoline-3-heptanoic acid, tert-Butyl ester (6) $m = 0, n = 5, p = 4, Q = CH_3, R = C(CH_3)_3, R_1 = R_2 = H$

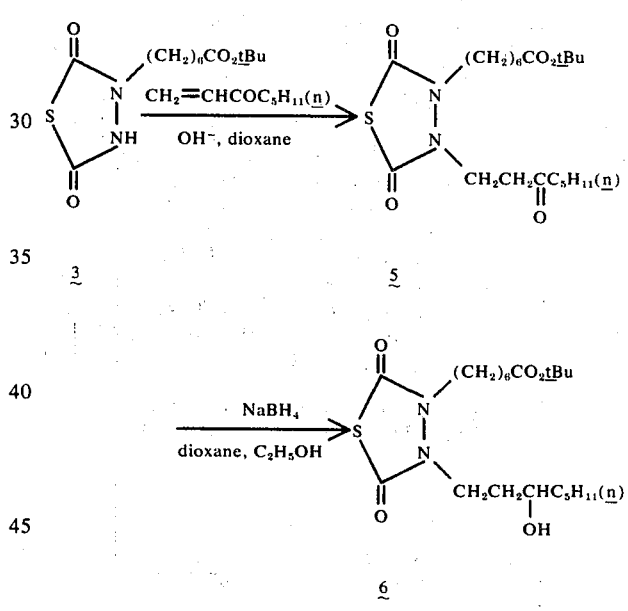

3

5

6

By a procedure analogous to that used in Example 1, Part C, 6.50 g (21.5 mmole) 2,5-dioxo-1,3,4-thiadiazline-3-heptanoic acid tert-butyl ester was treated with 3.5 g (28 mmole) of amyl vinyl ketone in 75 ml of dioxane in the presence of a trace of benzyltrimethylammonium hydroxide. The reduction of the intermediate ketone was accomplished without its isolation by adding ethanol (80 ml) and sodium borohydride (0.32 g, 8.4 mmole), followed by isolation of the crude product as previously described. Chromatography of the crude product (7.2g) on 200 g of Silicar CC7 silica gel gave on elution with chloroform 5.6 g of 4-(3-hydroxy-octyl)-2,5-dioxo-1,3,4-thiadiazoline-3-heptanoic acid tert-butyl ester as an oil, Ir, $v_{max}$ 1735 ($CO_2C(CH_3)_3$) and 1670 $cm^{-1}$ (amide), pmr, δ 1.42 ppm (s, 9H, $C(CH_3)_3$), HRMS, m/e calculated for $C_{21}H_{38}N_2O_5S$ ($M^+$): 430.2499; measured: 430.2506.

In Examples 1 and 2 when ethyl 7-bromoheptanoate of Example 1, Part B, or tert-butyl 7-bromoheptanoate of Example 2, Part A is substituted by a molar equivalent of the omega-halo ester of Column A of Table I, the product obtained is the corresponding ester of Column B of Table I. Reaction of the ester of Column B with one of the alkyl vinyl ketones of Column C as in Example 1, Part C, and Example 2, Part B, gives the 4-oxoalkyl-2,5-dioxo-1,3,4-thiadiazoline ester of Column D. Reduction of the keto ester of Column D with sodium borohydride as in Example 1, Part C, and Example 2, Part B, gives the corresponding 4-hydroxyalkyl-2,5-dioxo-1,3,4-thiadiazoline ester of Column E.

Table I

Preparation of Selected 4-(3-Hydroxyalkyl)-2,5-dioxo-1,3,4-thiadiazoline-3-alkanoic acid Esters*

| COLUMN A | COLUMN B |
|---|---|
| 1. $I(CH_2)_7CO_2\underline{t}\text{-Bu}$ | 1. 2,5-dioxo-1,3,4-thiadiazoline with $N\text{-}(CH_2)_7CO_2\underline{t}\text{-Bu}$ |
| 2. $I(CH_2)_6CO_2Et$ | 2. 2,5-dioxo-1,3,4-thiadiazoline with $N\text{-}(CH_2)_6CO_2Et$ |
| 3. $I(CH_2)_6CO_2\underline{t}\text{-Bu}$ | 3. 2,5-dioxo-1,3,4-thiadiazoline with $N\text{-}(CH_2)_6CO_2\underline{t}\text{-Bu}$ |
| 4. $I(CH_2)_6CO_2$-cyclopentyl | 4. 2,5-dioxo-1,3,4-thiadiazoline with $N\text{-}(CH_2)_6CO_2$-cyclopentyl |
| 5. $Br(CH_2)_6CO_2$-cyclohexyl | 5. 2,5-dioxo-1,3,4-thiadiazoline with $N\text{-}(CH_2)_6CO_2$-cyclohexyl |
| 6. $I(CH_2)_6CO_2\underline{n}\text{-}C_{10}H_{21}$ | 6. 2,5-dioxo-1,3,4-thiadiazoline with $N\text{-}(CH_2)_6CO_2\underline{n}\text{-}C_{10}H_{21}$ |
| 7. $Br(CH_2)_3CO_2\underline{n}\text{-}C_5H_{11}$ | 7. 2,5-dioxo-1,3,4-thiadiazoline with $N\text{-}(CH_2)_3CO_2\underline{n}\text{-}C_5H_{11}$ |

Table I-continued
Preparation of Selected 4-(3-Hydroxyalkyl)-2,5-dioxo-1,3,4-thiadiazoline-3-alkanoic acid Esters"
8. 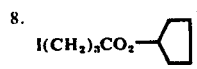 8. 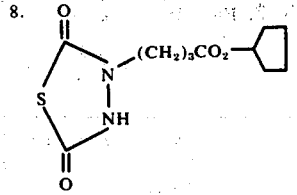
9. BrCH₂CH=CH(CH₂)₃CO₂CH₃ 9. 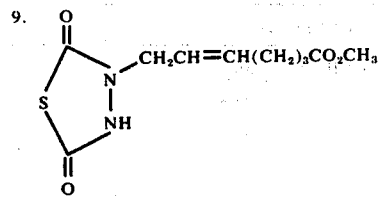
10. BrCH₂CH=CH(CH₂)₃CO₂Et 10. 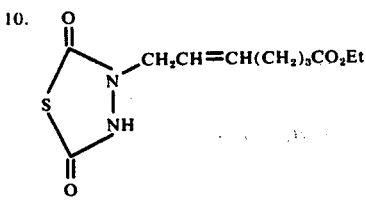
11. BrCH₂CH=CH(CH₂)₃CO₂t-Bu 11. 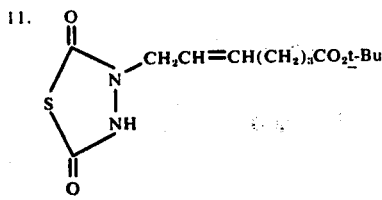
12. ICH₂CH=CH(CH₂)₃CO₂iPr 12. 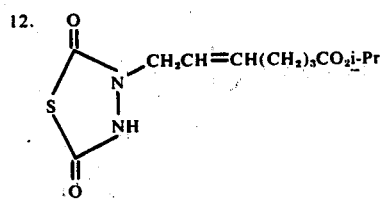
13. ICH₂C≡C(CH₂)₃CO₂CH₃ 13. 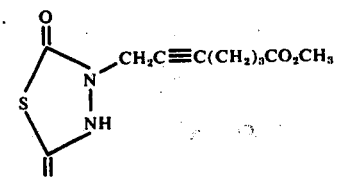
14. ICH₂C≡C(CH₂)₃CO₂Et 14. 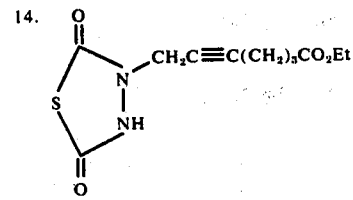
15. BrCH₂C≡C(CH₂)₃CO₂t-Bu 15. 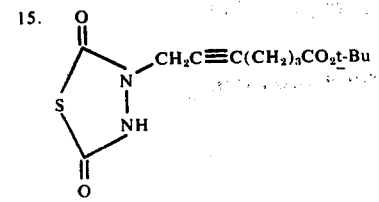

Table I-continued

Preparation of Selected 4-(3-Hydroxyalkyl)-
2,5-dioxo-1,3,4-thiadiazoline-3-alkanoic acid
Esters[a]

| # | Starting Material | # | Product |
|---|---|---|---|
| 16. | 2-(ClCH₂)C₆H₄-(CH₂)₂CO₂CH₃ | 16. | 4-[2-((CH₂)₂CO₂CH₃)benzyl]-2,5-dioxo-1,3,4-thiadiazolidine |
| 17. | 2-(BrCH₂)C₆H₄-(CH₂)₃CO₂t-Bu | 17. | 4-[2-((CH₂)₃CO₂t-Bu)benzyl]-2,5-dioxo-1,3,4-thiadiazolidine |
| 18. | 3-(BrCH₂)C₆H₄-(CH₂)₂CO₂t-Bu | 18. | 4-[3-((CH₂)₂CO₂t-Bu)benzyl]-2,5-dioxo-1,3,4-thiadiazolidine |
| 19. | 3-(ClCH₂)C₆H₄-(CH₂)₃CO₂Et | 19. | 4-[3-((CH₂)₃CO₂Et)benzyl]-2,5-dioxo-1,3,4-thiadiazolidine |
| 20. | 4-(BrCH₂)C₆H₄-(CH₂)₂CO₂CH₃ | 20. | 4-[4-((CH₂)₂CO₂CH₃)benzyl]-2,5-dioxo-1,3,4-thiadiazolidine |
| 21. | 4-(ClCH₂)C₆H₄-(CH₂)₄CO₂Et | 21. | 4-[4-((CH₂)₄CO₂Et)benzyl]-2,5-dioxo-1,3,4-thiadiazolidine |
| 22. | 4-(BrCH₂)C₆H₄-(CH₂)₃CO₂i-Pr | 22. | 4-[4-((CH₂)₃CO₂i-Pr)benzyl]-2,5-dioxo-1,3,4-thiadiazolidine |
| 23. | 4-(ClCH₂)C₆H₄-(CH₂)₄CO₂t-Bu | 23. | 4-[4-((CH₂)₄CO₂t-Bu)benzyl]-2,5-dioxo-1,3,4-thiadiazolidine |

Table I-continued
Preparation of Selected 4-(3-Hydroxyalkyl)-2,5-dioxo-1,3,4-thiadiazoline-3-alkanoic acid Esters
24. 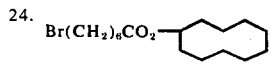  24. 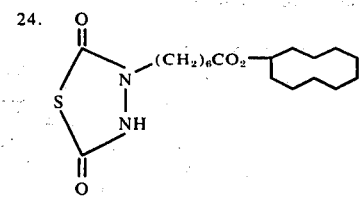
COLUMN C
1. $CH_2=CHCO(CH_2)_7CH_3$
2. $CH_2=CHCO(CH_2)_4CH_3$
3. $CH_2=CHCOCF_2CH_2CH_3$
4. $CH_2=CHCO(CH_2)_3CF_2CH_3$
5. $CH_2=CHCO(CH_2)_4CF_3$
6. $CH_2=CHCO(CH_2)_6CH_3$
COLUMN C
7. $CH_2=CHCOCF_2(CH_2)_4CH_3$
8. $CH_2=CHCOCHFCH_2CF_2CH_3$
9. $CH_2=CHCOCH_3$
10. $CH_2=CHCO(CH_2)_2CF_3$
11. $CH_2=CHCOC(CH_3)_2(CH_2)_3CH_3$
12. $CH_2=CHCOCH(CH_3)(CH_2)_3CH_3$
COLUMN D
1a. 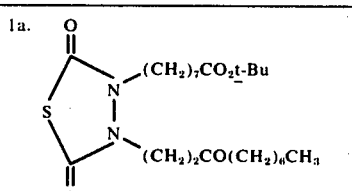
1b. 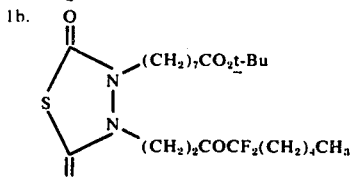
2a. 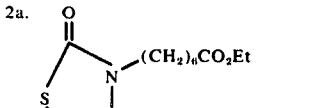
2b. 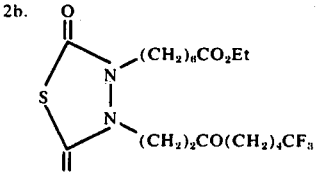
2c. 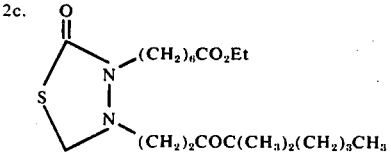
2d. 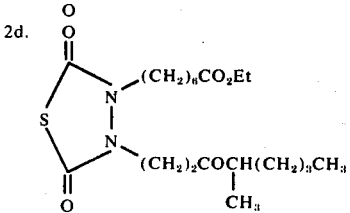
COLUMN E
1a. 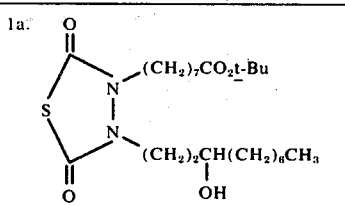
1b. 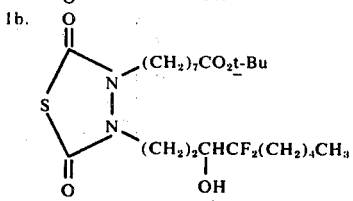
2a. 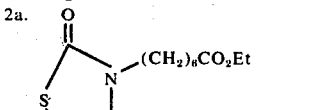
2b. 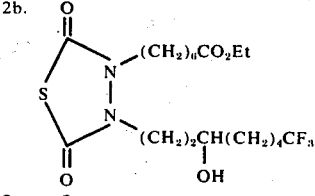
2c. 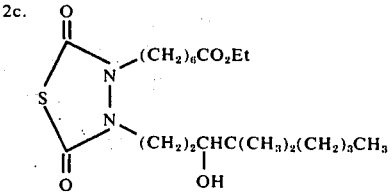
2d. 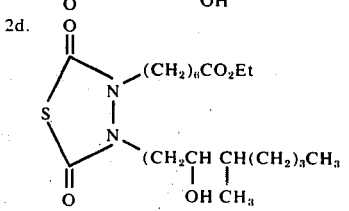

Table I-continued
Preparation of Selected 4-(3-Hydroxyalkyl)-
2,5-dioxo-1,3,4-thiadiazoline-3-alkanoic acid
Esters[a]
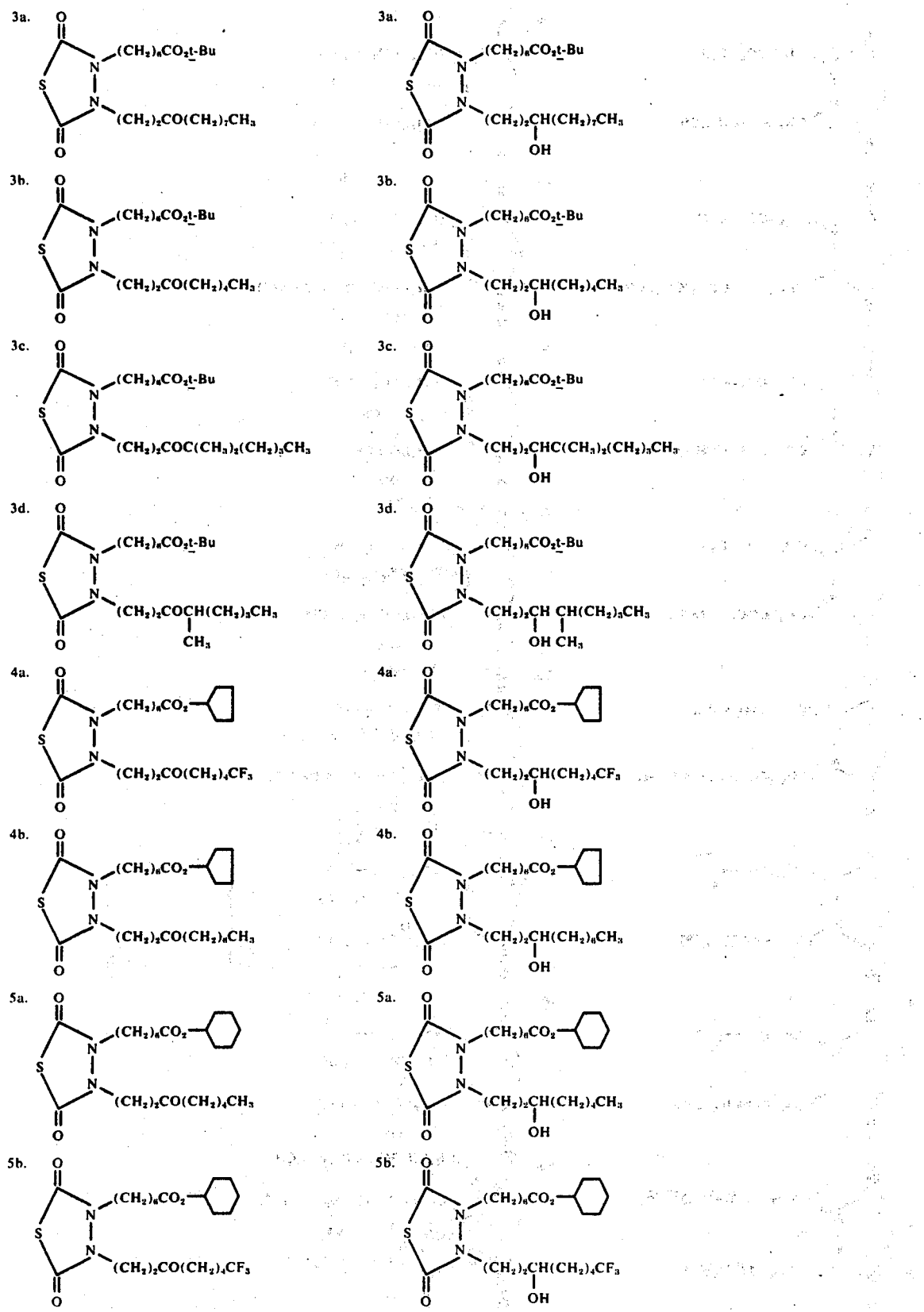

Table I-continued

Preparation of Selected 4-(3-Hydroxyalkyl)-2,5-dioxo-1,3,4-thiadiazoline-3-alkanoic acid Esters[a]

6a.

$$\text{thiadiazoline-N-(CH}_2)_6\text{CO}_2\underline{n}\text{-C}_{10}\text{H}_{21}$$
$$\text{N-(CH}_2)_2\text{CO(CH}_2)_4\text{CH}_3$$

6a.

$$\text{thiadiazoline-N-(CH}_2)_6\text{CO}_2\underline{n}\text{-C}_{10}\text{H}_{21}$$
$$\text{N-(CH}_2)_2\text{CH(CH}_2)_4\text{CH}_3$$
$$\text{OH}$$

6b.

$$\text{N-(CH}_2)_6\text{CO}_2\underline{n}\text{-C}_{10}\text{H}_{21}$$
$$\text{N-(CH}_2)_2\text{COC(CH}_3)_2(\text{CH}_2)_3\text{CH}_3$$

6b.

$$\text{N-(CH}_2)_6\text{CO}_2\underline{n}\text{-C}_{10}\text{H}_{21}$$
$$\text{N-(CH}_2)_2\text{CHC(CH}_3)_2(\text{CH}_2)_3\text{CH}_3$$
$$\text{OH}$$

6c.

$$\text{N-(CH}_2)_6\text{CO}_2\underline{n}\text{-C}_{10}\text{H}_{21}$$
$$\text{N-(CH}_2)_2\text{COCH(CH}_2)_3\text{CH}_3$$
$$\text{CH}_3$$

6c.

$$\text{N-(CH}_2)_6\text{CO}_2\underline{n}\text{-C}_{10}\text{H}_{21}$$
$$\text{N-(CH}_2)_2\text{CH CH(CH}_2)_3\text{CH}_3$$
$$\text{OH CH}_3$$

7a.

$$\text{N-(CH}_2)_3\text{CO}_2\underline{n}\text{-C}_8\text{H}_{11}$$
$$\text{N-(CH}_2)_2\text{COCF}_2\text{CH}_2\text{CH}_3$$

7a.

$$\text{N-(CH}_2)_3\text{CO}_2\underline{n}\text{-C}_8\text{H}_{11}$$
$$\text{N-(CH}_2)_2\text{CHCF}_2\text{CH}_2\text{CH}_3$$
$$\text{OH}$$

7b.

$$\text{N-(CH}_2)_3\text{CO}_2\underline{n}\text{-C}_8\text{H}_{11}$$
$$\text{N-(CH}_2)_2\text{COCHFCH}_2\text{CF}_2\text{CH}_3$$

7b.

$$\text{N-(CH}_2)_3\text{CO}_2\underline{n}\text{-C}_8\text{H}_{11}$$
$$\text{N-(CH}_2)_2\text{CHCHFCH}_2\text{CF}_2\text{CH}_3$$
$$\text{OH}$$

8a.

$$\text{N-(CH}_2)_3\text{CO}_2\text{-cyclopentyl}$$
$$\text{N-(CH}_2)_2\text{CO(CH}_2)_7\text{CH}_3$$

8a.

$$\text{N-(CH}_2)_3\text{CO}_2\text{-cyclopentyl}$$
$$\text{N-(CH}_2)_2\text{CH(CH}_2)_7\text{CH}_3$$
$$\text{OH}$$

8b.

$$\text{N-(CH}_2)_3\text{CO}_2\text{-cyclopentyl}$$
$$\text{N-(CH}_2)_2\text{CO(CH}_2)_4\text{CH}_3$$

8b.

$$\text{N-(CH}_2)_3\text{CO}_2\text{-cyclopentyl}$$
$$\text{N-(CH}_2)_2\text{CH(CH}_2)_4\text{CH}_3$$
$$\text{OH}$$

9a.

$$\text{N-CH}_2\text{CH}=\text{CH(CH}_2)_3\text{CO}_2\text{CH}_3$$
$$\text{N-(CH}_2)_2\text{CO(CH}_2)_4\text{CH}_3$$

9a.

$$\text{N-CH}_2\text{CH}=\text{CH(CH}_2)_3\text{CO}_2\text{CH}_3$$
$$\text{N-(CH}_2)_2\text{CH(CH}_2)_4\text{CH}_3$$
$$\text{OH}$$

Table I-continued
Preparation of Selected 4-(3-Hydroxyalkyl)-2,5-dioxo-1,3,4-thiadiazoline-3-alkanoic acid Esters"
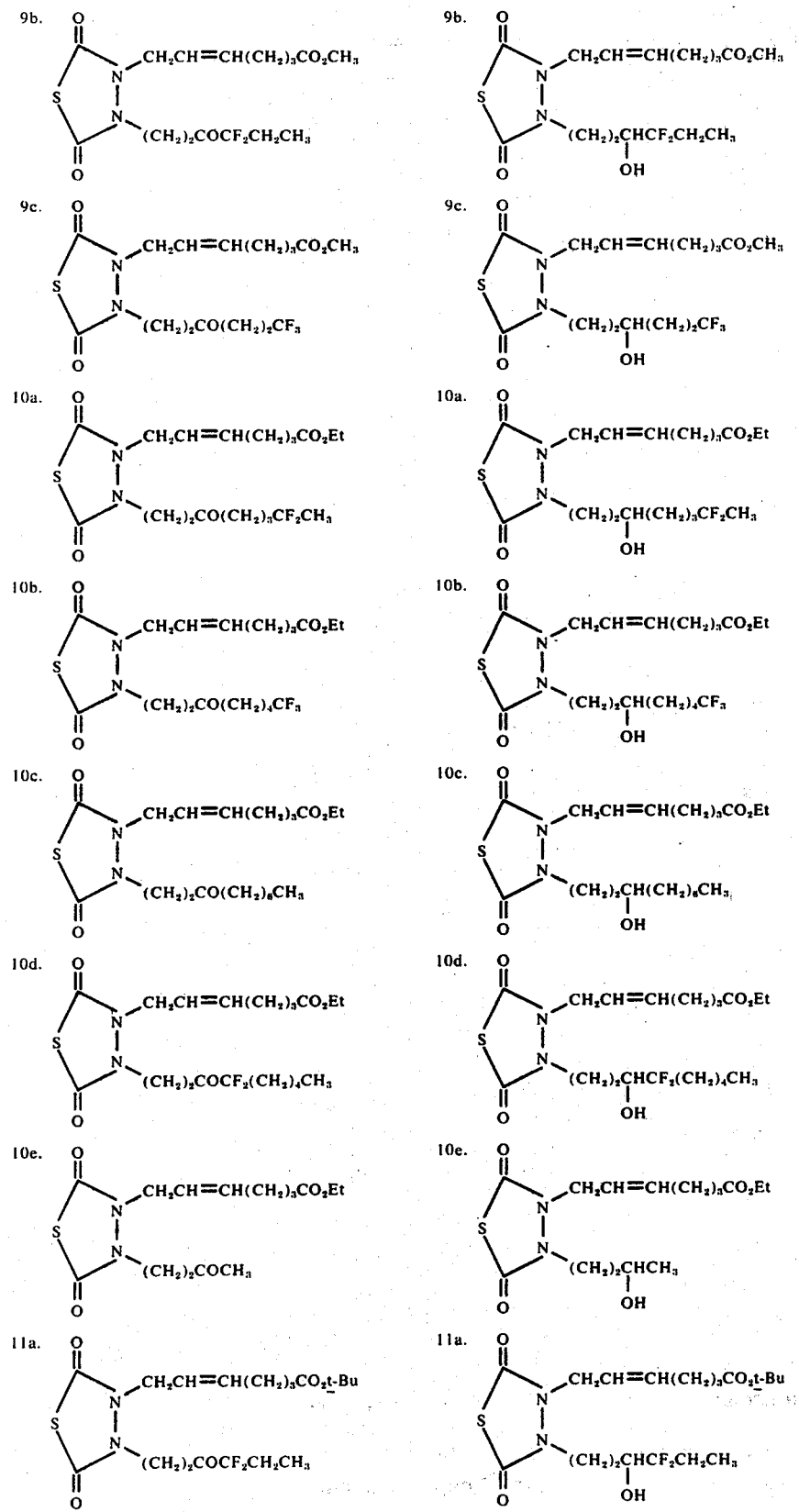

Table I-continued

Preparation of Selected 4-(3-Hydroxyalkyl)-2,5-dioxo-1,3,4-thiadiazoline-3-alkanoic acid Esters

| # | Ketone precursor | # | Hydroxy product |
|---|---|---|---|
| 11b. | 4-[CH₂CH=CH(CH₂)₃CO₂t-Bu], 3-[(CH₂)₂CO(CH₂)₃CF₂CH₃] thiadiazoline-2,5-dione | 11b. | 4-[CH₂CH=CH(CH₂)₃CO₂t-Bu], 3-[(CH₂)₂CH(OH)(CH₂)₃CF₂CH₃] thiadiazoline-2,5-dione |
| 11c. | 4-[CH₂CH=CH(CH₂)₃CO₂t-Bu], 3-[(CH₂)₂CO(CH₂)₄CF₃] | 11c. | 4-[CH₂CH=CH(CH₂)₃CO₂t-Bu], 3-[(CH₂)₂CH(OH)(CH₂)₄CF₃] |
| 12a. | 4-[CH₂CH=CH(CH₂)₃CO₂i-Pr], 3-[(CH₂)₂CO(CH₂)₇CH₃] | 12a. | 4-[CH₂CH=CH(CH₂)₃CO₂i-Pr], 3-[(CH₂)₂CH(OH)(CH₂)₇CH₃] |
| 12b. | 4-[CH₂CH=CH(CH₂)₃CO₂i-Pr], 3-[(CH₂)₂COCF₂(CH₂)₄CH₃] | 12b. | 4-[CH₂CH=CH(CH₂)₃CO₂i-Pr], 3-[(CH₂)₂CH(OH)CF₂(CH₂)₄CH₃] |
| 13a. | 4-[CH₂C≡C(CH₂)₃CO₂CH₃], 3-[(CH₂)₂CO(CH₂)₇CH₃] | 13a. | 4-[CH₂C≡C(CH₂)₃CO₂CH₃], 3-[(CH₂)₂CH(OH)(CH₂)₇CH₃] |
| 13b. | 4-[CH₂C≡C(CH₂)₃CO₂CH₃], 3-[(CH₂)₂CO(CH₂)₄CH₃] | 13b. | 4-[CH₂C≡C(CH₂)₃CO₂CH₃], 3-[(CH₂)₂CH(OH)(CH₂)₄CH₃] |
| 13c. | 4-[CH₂C≡C(CH₂)₃CO₂CH₃], 3-[(CH₂)₂COCF₂CH₂CH₃] | 13c. | 4-[CH₂C≡C(CH₂)₃CO₂CH₃], 3-[(CH₂)₂CH(OH)CF₂CH₂CH₃] |
| 14a. | 4-[CH₂C≡C(CH₂)₃CO₂Et], 3-[(CH₂)₂CO(CH₂)₇CH₃] | 14a. | 4-[CH₂C≡C(CH₂)₃CO₂Et], 3-[(CH₂)₂CH(OH)(CH₂)₇CH₃] |

Table I-continued
Preparation of Selected 4-(3-Hydroxyalkyl)-2,5-dioxo-1,3,4-thiadiazoline-3-alkanoic acid Esters
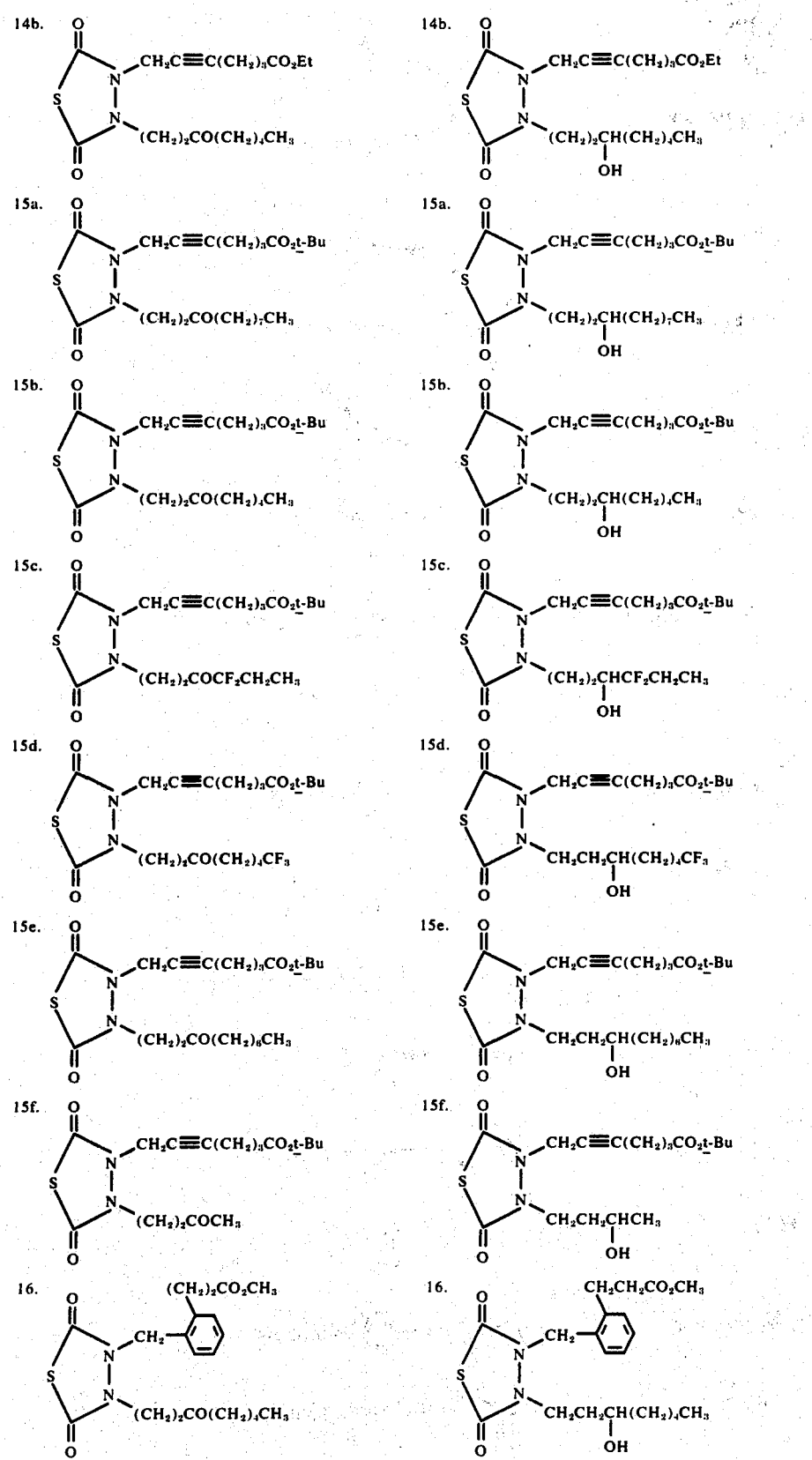

Table I-continued
Preparation of Selected 4-(3-Hydroxyalkyl)-
2,5-dioxo-1,3,4-thiadiazoline-3-alkanoic acid
Esters"
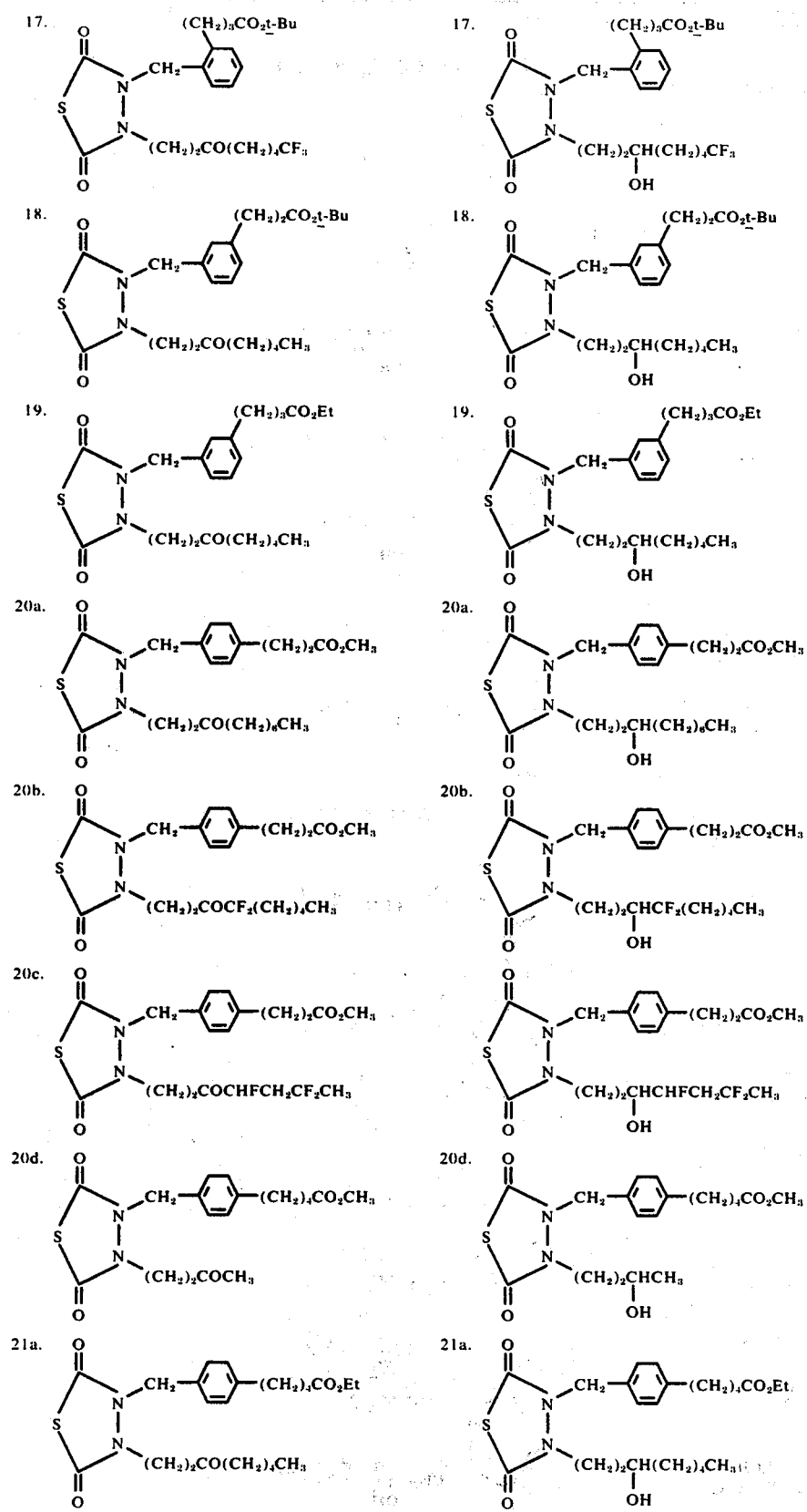

Table I-continued
Preparation of Selected 4-(3-Hydroxyalkyl)-2,5-dioxo-1,3,4-thiadiazoline-3-alkanoic acid Esters[a]
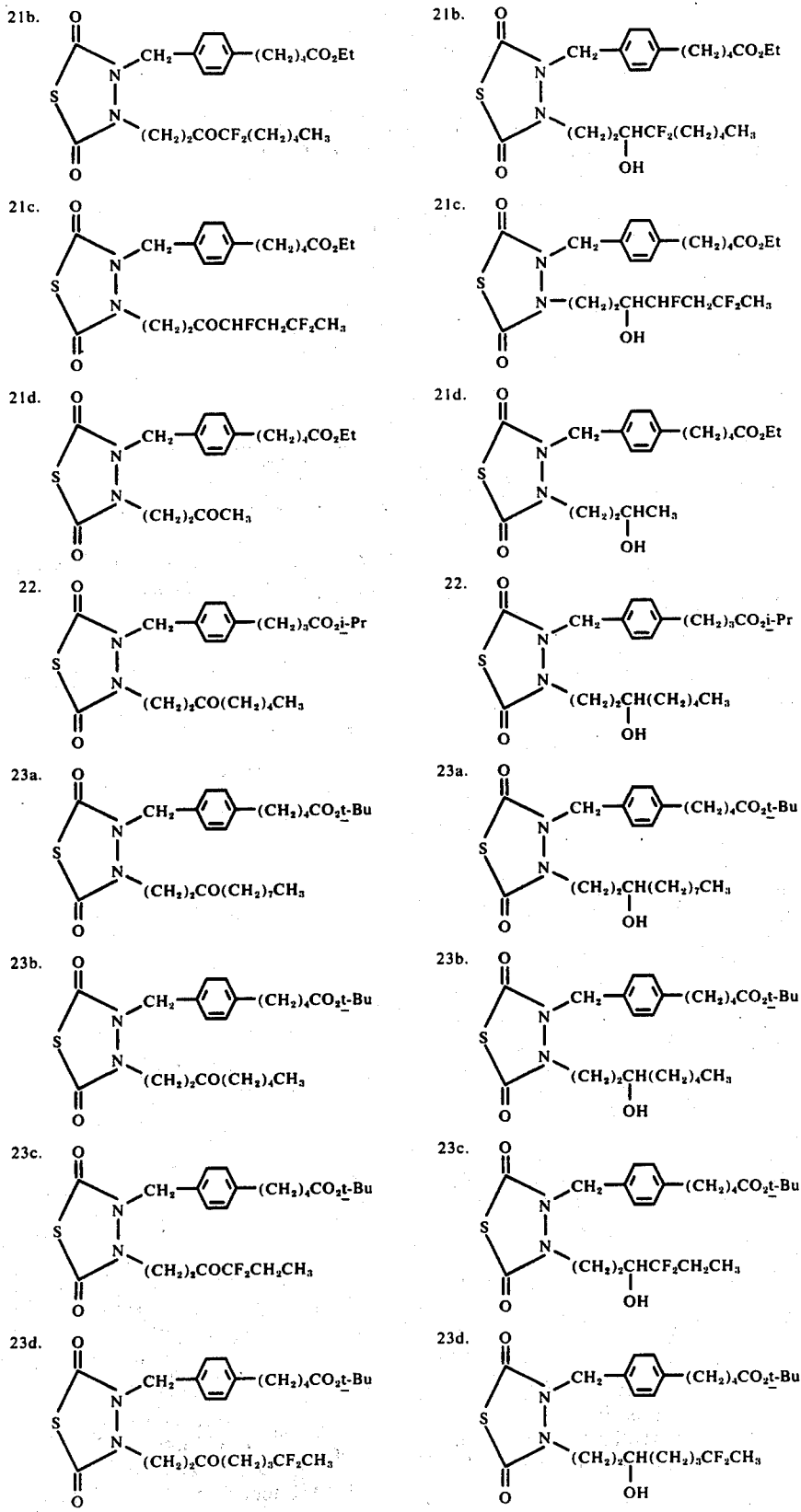

Table I-continued

Preparation of Selected 4-(3-Hydroxyalkyl)-2,5-dioxo-1,3,4-thiadiazoline-3-alkanoic acid Esters[a]

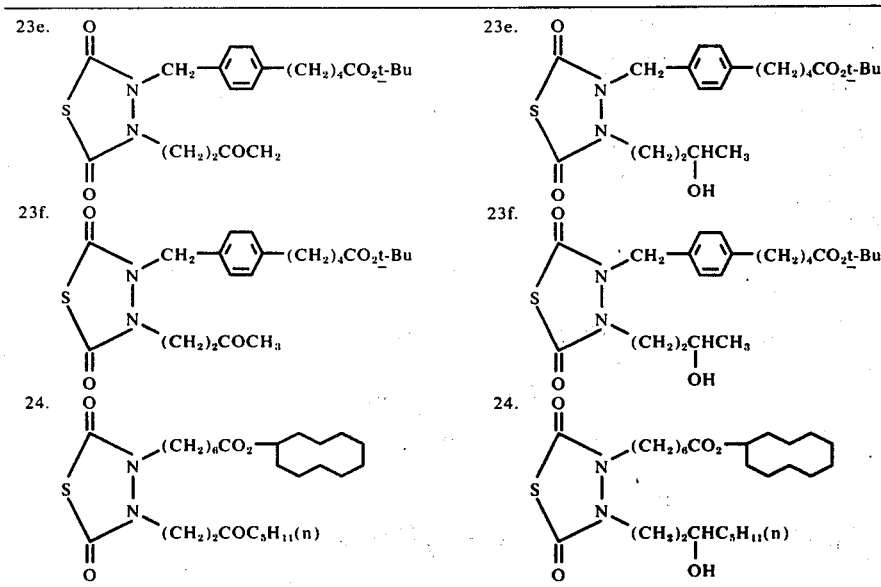

HMPA

[a]For brevity, "alkanoic" in the heading also includes "alkenoic", "alkynoic", and "methylenebenzenealkanoic". In the Table, Et denotes $C_2H_5$, i-Pr denotes $(CH_3)_2CH$, and t-Bu denotes $(CH_3)_3C$. Carbon-carbon double bonds may be cis or trans; the preferred isomer is the cis compound.

Some of the halocarboxylates (2) of the structure $XCH_2(A)_m(CH_2)_nCO_2R$ are commercially available while others can be made from the corresponding omega-bromo or chloro acids and the appropriate alcohol using conventional methods for esterification (see for example C. Buehler and D. Pearson, *Survey of Organic Synthesis*, Wiley-Interscience, N. Y. 1970, Chap. 14).

| n | $XCH_2(CH_2)_nCO_2R$ |
|---|---|
| 0 | methyl iodoacetate |
| 1 | ethyl β-bromopropionate |
| 2 | t-butyl 4-bromopropionate |
| 2 | t-butyl 4-chloropropionate |
| 2 | p-chlorobenzyl 4-bromobutyrate |
| 3 | methyl 5-bromobutyrate |
| 3 | n-octyl 5-bromovalerate |
| 3 | iso-octyl 5-chlorovalerate |
| 4 | isopropyl 6-bromohexanoate |
| 4 | valeryl 6-bromohexanoate |
| 4 | tert-butyl 6-bromohexanoate |
| 5 | ethyl 7-bromoheptanoate |
| 5 | t-butyl 7-iodoheptanoate |
| 5 | cyclopentyl 7-bromoheptanoate |
| 5 | cyclohexyl 7-bromoheptanoate |
| 5 | 3-phenylpropyl 7-bromoheptanoate |
| 5 | n-dodecyl 7-bromoheptanoate |
| 6 | t-butyl 8-bromooctanoate |

The iodo esters are made by Finkelstein halide interchange (Buehler and Pearson, ibid., page 339) (NaI in acetone) with the corresponding bromo ester, or, the bromo esters can be used directly for the preparation of the 2-alkanoate derivatives in the presence of sodium iodide, which generates the more reactive iodo ester in situ. The bromo esters also alkylate 1 of Example 1, Part B, in the absence of sodium iodide, but more slowly. Dimethylsulfoxide can be used as the solvent, but hexamethylphosphoric triamide (HMPA) is preferred.

The corresponding acids $XCH_2(C_6H_4)(CH_2)_nCO_2H$ are prepared by chloromethylation or bromomethylation of the omega-arylalkanoic acids.

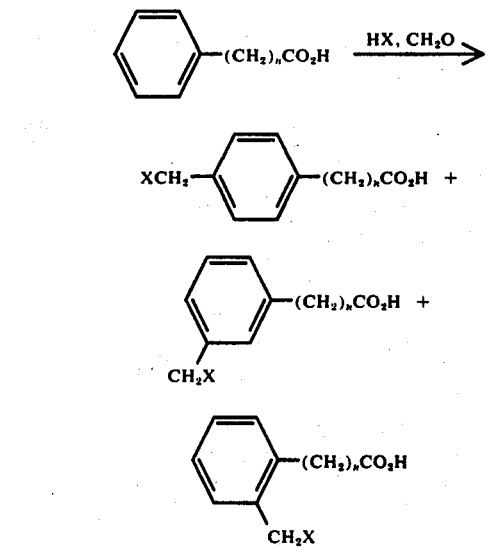

Mixtures of the o, m, and p-isomers are produced by these reactions [I. N. Nazarov et al., Bull. Acad. Sci. USSR, Div. Chem. Sci. 103 (1957)] and the preferred p-isomers are readily isolated by fractional crystallization. From the mother liquors of such crystallizations the corresponding ortho and meta isomers can be isolated by column chromatography or, in the case of their methyl ester derivatives, by preparative gas chromatography.

Chloromethylation is best carried out in the presence of zinc chloride (see G. A. Olah and W. S. Tolygyese in Olah, *Friedel-Crafts and Related Reactions*, Vol. II, part 2, Chapter XXI, Interscience, 1964). The benzyl chlorides are readily converted to the corresponding benzyl iodides by the action of NaI in acetone.

Although bromomethylation is reported to give less satisfactory yields than chloromethylation (*Organic Reactions*, Vol. I, Chap. 3, p. 72, Wiley and Sons, N. Y. 1942), in the case of the omega-phenylalkanoic acids, bromomethylation has been found more convenient. The benzyl bromides obtained are better N-alkylating agents than the corresponding benzyl chlorides, and they need not be converted to the corresponding relatively unstable benzyl iodides before reaction with structure 1 as in Example 1, Part B. Better yields of bromomethylation products are obtained when the reactions are carried out in the absence of added zinc salts.

The omega-(halomethyl)alkanoic acids can be converted to their alkyl esters, for example, by reaction with diazoalkanes in ether or by Fisher (acid catalyzed) esterification with alcohols:

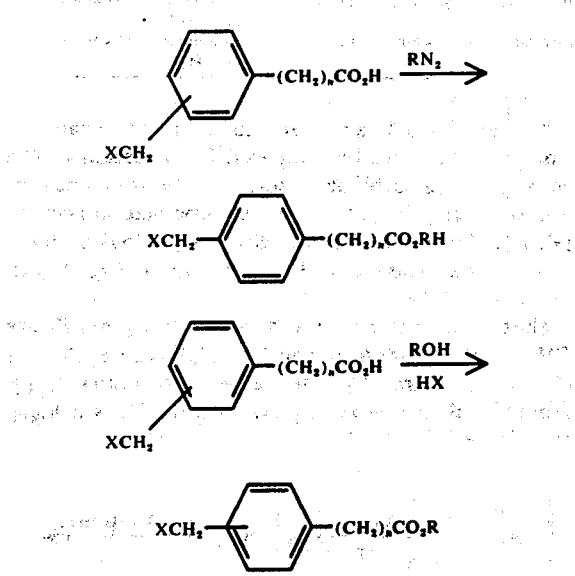

In the latter case yields are increased by using an excess of the alcohol and a drying agent, e.g., 3A or 4A molecular sieves, can be used. t-Butyl esters can be made from reaction of the acids with isobutylene in the presence of sulfuric acid.

Omega-halocarboxylic esters wherein A is C ≡ C or CH=CH (i.e., m=1) are obtainable as follows. By using homologs of the known acetylenic ester, methyl 7-iodoheptynoate $XCH_2C \equiv C(CH_2)_nCO_2CH_3$ (X=I, n = 3, R = CH$_3$) [Ferdinandi and Just, Can. J. Chem. 49, 1070 (1971)] an ester of the first column below gives by the analogous sequence of reactions a corresponding acetylenic ester of the second column below, where the halogen is either bromo or iodo depending on whether the metal halide is LiBr or NaI.

| Ester | Acetylenic Ester |
|---|---|
| n = 1, ethyl bromoacetate | ethyl 5-halopent-3-ynoate |
| n = 2, ethyl 3-bromopropionate | propyl 6-halohex-4-ynoate |
| n = 3, ethyl 4-bromobutyrate | methyl 7-halohept-5-ynoate |

For the synthesis of ethyl 4-halobut-2-ynoate, the case where n is zero, the following synthetic sequence can be used, starting with ethyl propiolate.

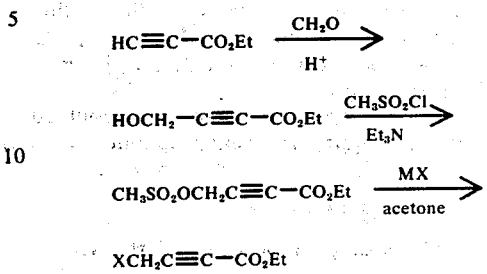

Omega-halo carboxylic esters wherein m=1 and A is cis CH=CH are available by hydrogenation of the above described acetylenic esters (A is C ≡ C) over Lindlar catalyst or over Ni$_2$B catalyst. Lindlar catalyst [H. Lindlar, Helv. Chim. Acta, 35, 446 (1952)] is palladium on calcium carbonate which has been deactivated by addition of lead acetate and quinoline. This catalyst is inactive toward hydrogenation of olefins, and the hydrogenation of acetylenes over this material practically stops after absorption of one mole of hydrogen. Palladium on barium sulfate with synthetic quinoline is a similar catalyst but it is somewhat superior in reproducibility and ease of preparation [D. J. Cram and N. L. Allinger, J. Am. Chem. Soc., 78, 2518 (1956)]. Both catalysts give olefins of the cis configuration. Alternatively, nickel boride catalyst (Ni$_2$B), especially that designated P-2 [H. C. Brown and C. A. Brown, J. Am. Chem. Soc., 85, 1005 (1963)] also effects catalytic reduction of the acetylenic compounds of cis olefins. J. Martel and E. Toromonoff in U.S. Pat. No. 3,806,540 (1974) also describe the preparation of esters having the formula XCH$_2$CH=CH-(CH$_2$)$_n$CO$_2$Alk (cis) and XCH$_2$C ≡ C(CH$_2$)$_n$CO$_2$Alk, where Alk is alkyl of 1 to 7 carbon atoms.

The following examples illustrate some of the above procedures.

EXAMPLE 3

4-(Bromomethyl)benzenepropionic Acid, Methyl Ester

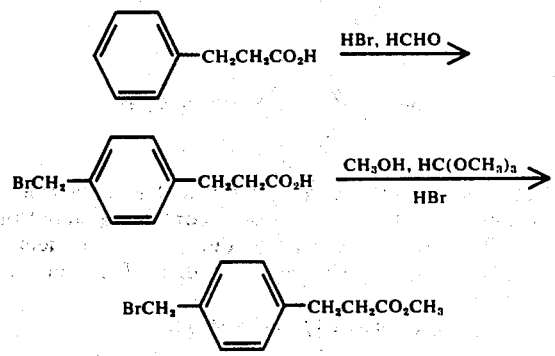

β-Phenylpropionic acid (150 g, 1.0 mole) is bromomethylated by passing HBr gas into a mixture of the acid, paraformaldehyde (40g), and 48 percent aqueous HBr (200 ml) at 50°-55° for 3.5 hrs. This gives a mixture of ortho, meta, and para(bromomethyl)benzenepropionic acids from which the para isomer can be isolated by recrystallization from CCl$_4$. The 4-

(bromomethyl)benzenepropionic acid obtained (100 g, 41%) melts at 133°–316°.

Anal. Calcd. for $C_{10}H_{11}BrO_2$: C, 49.4; H, 4.55; Br, 32.9. Found: C, 49.67; H, 4.78; Br, 33.05.

The bromoacid (50 g) is converted to the methyl ester in methanol (300 ml) and methyl orthoformate (20 ml) with anhydrous HBr as the catalyst giving 4-(bromomethyl)benzenepropionic acid methyl ester (42.5 g) m.p. 38°–42° (hexane); it contains about 20 percent 4-(methoxymethyl)benzenepropionic acid methyl ester, according to pmr spectroscopy.

EXAMPLE 4

4-(Bromomethyl)benzenebutyric Acid, Methyl Ester

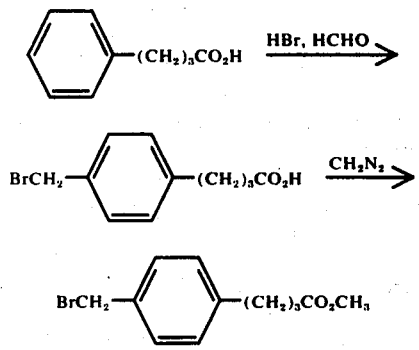

4-Phenylbutyric acid (150 g) is bromomethylated in 200 ml of 48 percent HBr with 36 g paraformaldehyde and gaseous HBr for 3.5 hrs at 60°–65°, and then without addition of HBr for 1.5 hrs at 70°–75°, giving a mixture of ortho, meta, and para isomers from which pure 4-(bromomethyl)benzenebutyric acid, m.p 137°–138° is isolated by recrystallization from $CCl_4$. Treatment of the acid in ether-tetrahydrofuran with diazomethane gives the methyl ester of 4-(bromomethyl)benzenebutyric acid as a liquid.

EXAMPLE 5

4-(Bromomethyl)benzenebutyric Acid, iso-Propyl Ester

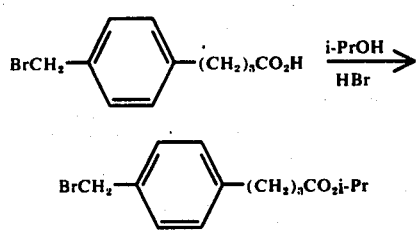

4-(Bromomethyl)benzenebutyric acid is converted to its isopropyl ester in isopropanol containing anhydrous HBr. The reaction is carried out over 4A molecular sieve at room temperature for 2 days. This ester is a colorless liquid.

The vinyl ketones (4) of the structure

are prepared by two general processes: (1) by reaction of vinyllithium (2 equivalents) with the appropriate carboxylic acid $Q(CH_2)_pCR_1R_2CO_2H$ (1 equivalent) in 1,2-dimethoxyethane according to the method described by J. C. Floyd in Tetrahedron Letters, 2877 (1974); or (2) by oxidation of the corresponding vinyl carbinols

which in turn are prepared by reaction of acrolein with suitable Gringnard reagents. In either case the crude vinyl ketone is purified by distillation and stored in the presence of a trace of a polymerization inhibitor such as p-methoxyphenol (0.2% by wt).

When $R_1$ and $R_2$ are H and Q is H or $CH_3$ these vinyl ketones are as follows:

| | |
|---|---|
| p=0 methyl vinyl ketone (Q=H) | p=3 amyl vinyl ketone (Q=CH₃) |
| p=0 ethyl vinyl ketone (Q=CH₃) | p=4 hexyl vinyl ketone (Q=CH₃) |
| p=1 propyl vinyl ketone (Q=CH₃) | p=5 heptyl vinyl ketone (Q=CH₃) |
| p=2 butyl vinyl ketone (Q=CH₃) | p=6 octyl vinyl ketone Q=CH₃) |

The first two ketones are commercially available. The others are readily prepared by oxidation of the corresponding carbinols. These oxidations can be carried out using $CrO_3$, $H_2O$, and sulfuric acid in acetone [K. Bowden, et al., J. Chem. Soc. 39 (1946)] or aqueous chromic acid/ether [H. C. Brown, J. Org. Chem. 36, 387 (1971)].

These vinyl ketones and those where $R_1$ and $R_2$ are $CH_3$ or ethyl, p=0 to 6, and Q is H, $CH_3$, $CF_2CH_3$, or $CF_3$, are prepared by a sequence of reactions represented by the following equations where X is halogen (Cl, Br, or I):

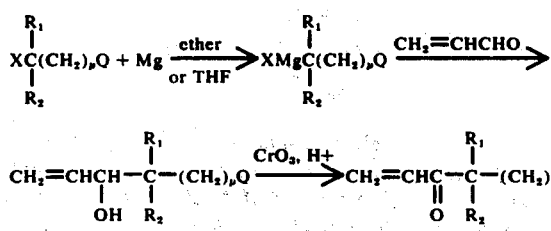

Thus, the Grignard reagent derived from the halo compound $XC(R_1R_2)(CH_2)_pQ$ is treated with acrolein to give a carbinol that on oxidation gives the vinyl ketone. The starting halo compounds are either known or available by conventional synthetic methods. Some typical syntheses of $XC(R_1R_2)(CH_2)_pQ$ are:

$Br(CH_2)_7CF_3$: from reaction of $Br(CH_2)_7CO_2H$ and $SF_4$ (see G. A. Boswell, Jr., W. C. Ripka, R. M. Scribner and C. W. Iullock, Organic Reactions, Vol. 21, W. G. Dauben, Editor, John Wiley and Sons, Inc., 1974).

$BrC(CH_3)_2(CH_2)_4CH_3$: from reaction of HBr with 2-methyl-2-heptanol.

$I(CH_2)_6CF_3$: from reaction of $I(CH_2)_6CO_2H$ and $SF_4$ (see G. A. Boswell, Jr., et al., loc. cit.).

$ClC(CH_3)_2(CH_2)_3CF_3$: from reaction of the Grignard reagent derived from $CF_3(CH_2)_3Br$ with acetone followed by reaction of the resulting tertiary carbinol with HCl.

ICH(CH₃) (CH₂)₂CF₂CH₃: from the reaction of 4-chloro-2-butanone with SF₄ to give 2,2-difluoro-4-chloro-butanone, followed by reaction of the Grignard reagent of the latter with acetaldehyde, and conversion of the resulting secondary alcohol to the mesylate; treatment of the mesylate with sodium iodide in acetone gives the difluoroalkyl iodide.

BrCH(CH₃) (CH₂)₂CH₃: from the action of carbon tetrabromide and triphenylphosphine on 2-pentanol.

ClC(C₂H₅)₂CH₂CH₃: from the action of HCl on triethylcarbinol.

Vinyl ketones of the structure CH₂=CHCOC(R₁R₂)(CH₂)ₚQ where R₁ and R₂ include fluorine are prepared by two alternate methods: (1) by reaction of the appropriate fluoroacyl chloride with ethylene followed by dehydrochlorination, or (2) by reaction of the appropriate fluoroaldehyde with vinyllithium followed by oxidation of the resulting carbinol to the ketone.

METHOD 1

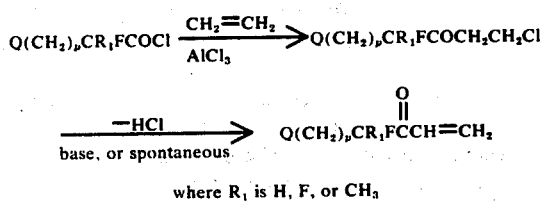

where R₁ is H, F, or CH₃

The synthesis of alkyl vinyl ketones by this kind of process is well known to take place in the presence of aluminum chloride, stannic chloride, or zinc chloride. The β-chloroketone addition product readily loses HCl either spontaneously or on mild alkaline treatment [Catch et al., *J. Chem. Soc.*, 278 (1948); Cologne and Mostafavi, *Bull. Soc. Chim. France*, 6 (5), 341 (1939)]. The fluoracids from which the acyl chlorides are prepared are either reported in the literature, or easily prepared by methods analogous to those described for the synthesis of closely-related fluoroacids. Several general methods for preparing α-fluoroacids are known [F. L. M. Pattison, et al., *Can. J. Chem.*, 43, 1700 (1965); E. Elkirk, et al., *Compt. Rend. Ser C*, 262 (9), 763 (1966); E. Elkirk, *Bull. Soc. Chim. France*, 2254 (1964)]. These acids are in turn smoothly converted to the corresponding acyl chlorides (for use in the Friedel-Crafts addition to ethylene) by the action of well-known reagents such as SOCl₂ or PCl₅ (see for example, Buehler and Pearson, *Survey of Organic Syntheses*, Wiley-Interscience, New York 1970, Chap. 15).

α,α-Difluoropropionic acid and α,α-difluorobutyric acid are examples of known α,α-difluoroalkanoic acids. The α,α-difluoroalkanoic acids can be made from reaction of sulfur tetrafluoride with the appropriate α-ketoalkanoic acid or the ester. If the reaction is carried out under mild conditions, e.g., at about 10° in CH₂Cl₂ solvent in the presence of HF catalyst, the keto group of the α-ketoalkanoic acid is converted to a gem-difluoro group, while the carboxylic acid group, and to a lesser extent the ester group, is converted to an acyl fluoride group. Hydrolysis of the α,α-difluoroacyl fluoride and/or the α,α-difluoroalkanoic ester, gives the α,α-difluoroalkanoic acid.

Using method 1 the acids of column I are converted through their acid chlorides to the vinyl ketones of column II.

| Column I | Column II |
|---|---|
| n-C₅H₁₁CF₂CO₂H | n-C₅H₁₁CF₂COCH=CH₂ |
| n-C₄H₉CF(CH₃)CO₂H | n-C₄H₉CF(CH₃)COCH=CH₂ |
| CF₃(CH₂)₃CHFCO₂H | CF₃(CH₂)₃CHFCOCH=CH₂ |
| CH₃CF₂CH₂CHFCO₂H | CH₃CF₂CH₂CHFCOCH=CH₂ |
| C₂H₅CF₂CO₂H | C₂H₅CF₂COCH=CH₂ |

METHOD 2

This synthesis of fluoroalkyl vinyl ketones can be represented by the following equations.

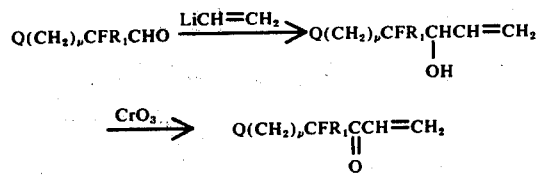

The starting fluoroaldehydes Q(CH₂)ₚCFR₁CHO can be made by conventional methods of organic synthesis. For example, reduction of fluoroalkanoic acids with LiAlH₄ or NaAlH—(OCH₂CH₂OCH₃)₂ provides the aldehydes (or their hydrates). Other methods for making α-fluoroaldehydes are known (e.g., J. Cantacuzine and D. Ricard, *Bull. Soc. Chim. France*, 1507 (1967); F. L. M. Pattison, loc. cit.), and in some cases these methods are more convenient than reduction of the fluoroalkanoic acids.

Using the vinyl lithium of method 2 the aldehydes of column III are converted in two steps to the vinyl ketones of column IV.

| Column III | Column IV |
|---|---|
| n-C₆H₁₃CHFCHO | C₆H₁₃CHFCCH=CH₂<br>‖<br>O |
| CF₃(CH₂)₄CHO | CF₃(CH₂)₄CCH=CH₂<br>‖<br>O |

EXAMPLE 6

4-(3-Hydroxyoctyl)-2,5-dioxo-1,3,4-thiadiazoline-3-heptanoic acid (8)

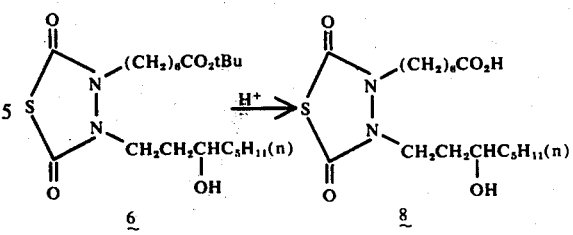

A solution of 1.95 g (4.5 mmole) of 4-(3-hydroxyoctyl)-2,5-dioxo-1,3,4-thiadiazoline-3-heptanoic acid tert-butyl ester (6) in 10 ml of trifluoroacetic acid was kept at 0° for 1.5 hr and then evaporated at 0° under vacuum. Benzene (75 ml) was added to the residue and the solution re-evaporated. The remaining oil was stirred with 100 ml of 5% NaHCO₃ for 1 hr and extracted with ether, the ether extract then being discarded. The remaining aqueous raffinate was then acidified with HCl and extracted with ether, giving 1.7 g of 4-(3-hydroxyoctyl)-2,5-dioxo-1,3,4-thiadiazoline-3-heptanoic acid (8); $R_f$=0.26 on silica gel, 1:1 $CHCl_3$—ether, $I_2$ visualization. Acid 8 was identified by its solubility in 5% $NaHCO_3$.

In Example 6, when 4-(3-hydroxyoctyl)-2,5-dioxo-1,3,4-thiadiazoline-3-heptanoic acid tert-butyl ester (6) is replaced by one of the tert-butyl esters of Table I, Column E, there is obtained the corresponding acid, analogous to 4-(3-hydroxyoctyl)-2,5-dioxo-1,3,4-thiadiazoline-3-heptanoic acid (8). The acids of this invention are listed in Table II, Column A. Table II, Column B lists representative salts of these acids, obtained by neutralization of the acid with an equivalent amount of the appropriate base in a suitable solvent by methods well known in the art. The sodium salts are obtained by neutralization of the acids with aqueous $NaHCO_3$; the potassium salts by neutralization of the acids with aqueous $KHCO_3$; the trimethylammonium salts by neutralization of the acids with ethanolic trimethylamine; and the tris-(hydroxymethyl)methylammonium salts by neutralization of the acids with ethanolic tris-(hydroxymethyl)aminomethane.

TABLE II

Selected 4-(3-hydroxyalkyl)-2,5-dioxo-1,3,4-thiadiazoline-3-alkanoic acids and Salts[a]

| | COLUMN A | COLUMN B |
|---|---|---|
| 1a. | (structure: thiadiazoline with $(CH_2)_7CO_2H$ and $(CH_2)_2CH(CH_2)_4CH_3$ with OH) | $Na, K, (CH_3)_3NH, (HOCH_2)_3CNH_3$ |
| 1b. | (structure: thiadiazoline with $(CH_2)_7CO_2H$ and $(CH_2)_2CHCF_2(CH_2)_4CH_3$ with OH) | " |
| 3a. | (structure: thiadiazoline with $(CH_2)_6CO_2H$ and $(CH_2)_2CH(CH_2)_7CH_3$ with OH) | " |
| 3b. | (structure: thiadiazoline with $(CH_2)_6CO_2H$ and $(CH_2)_2CH(CH_2)_4CH_3$ with OH) | " |
| 3c. | (structure: thiadiazoline with $(CH_2)_6CO_2H$ and $(CH_2)_2CHC(CH_3)_2(CH_2)_3CH_3$ with OH) | " |
| 3d. | (structure: thiadiazoline with $(CH_2)_6CO_2H$ and $(CH_2)_2CHCH(CH_2)_3CH_3$ with OH and $OCH_3$) | " |

TABLE II-continued
Selected 4-(3-hydroxyalkyl)-2,5-dioxo-1,3,4-thiadiazoline-3-alkanoic acids and Salts[a]
| | COLUMN A | COLUMN B |
|---|---|---|
| 11a. | 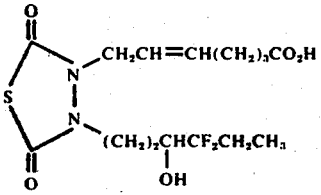 | " |
| 11b. | 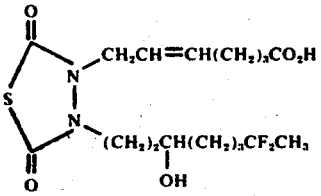 | " |
| 11c. | 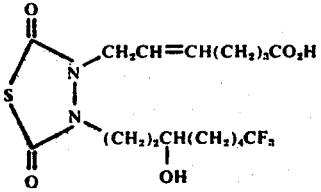 | " |
| 15a. | 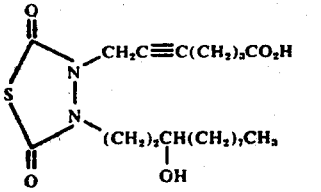 | " |
| 15b. | 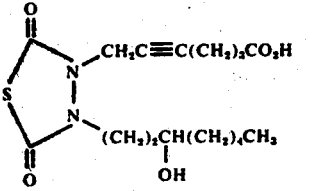 | " |
| 15c. | 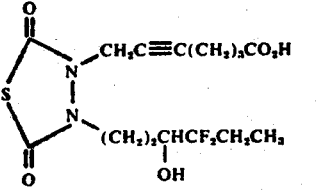 | " |
| 15d. | 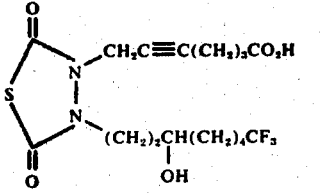 | " |
| 15e. | 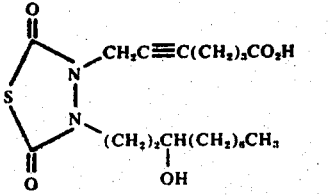 | " |

TABLE II-continued
Selected 4-(3-hydroxyalkyl)-2,5-dioxo-1,3,4-thiadiazoline-3-alkanoic acids, and Salts[a]

| | COLUMN A | COLUMN B |
|---|---|---|
| 15f. | N-$CH_2C\equiv C(CH_2)_3CO_2H$; N-$(CH_2)_2CHCH_3$ / $OH$ | " |
| 17. | N-$CH_2$-C$_6$H$_4$-$(CH_2)_3CO_2H$ (ortho); N-$(CH_2)_2CH(CH_2)_4CF_3$ / $OH$ | " |
| 18. | N-$CH_2$-C$_6$H$_4$-$(CH_2)_2CO_2H$ (meta); N-$(CH_2)_2CH(CH_2)_4CH_3$ / $OH$ | " |
| 23a. | N-$CH_2$-C$_6$H$_4$-$(CH_2)_4CO_2H$ (para); N-$(CH_2)_2CH(CH_2)_7CH_3$ / $OH$ | " |
| 23b. | N-$CH_2$-C$_6$H$_4$-$(CH_2)_4CO_2H$; N-$(CH_2)_2CH(CH_2)_4CH_3$ / $OH$ | " |
| 23c. | N-$CH_2$-C$_6$H$_4$-$(CH_2)_4CO_2H$; N-$(CH_2)_2CHCF_2CH_3$ / $OH$ | " |
| 23d. | N-$CH_2$-C$_6$H$_4$-$(CH_2)_4CO_2H$; N-$(CH_2)_2CH(CH_2)_3CF_2CH_3$ / $OH$ | " |
| 23e. | N-$CH_2$-C$_6$H$_4$-$(CH_2)_4CO_2H$; N-$(CH_2)_2CHCH_3$ / $OH$ | " |

TABLE II-continued

Selected 4-(3-hydroxyalkyl)-2,5-dioxo-1,3,4-thiadiazoline-3-alkanoic acids and Salts[a]

| COLUMN A | COLUMN B |
|---|---|
| 23f. 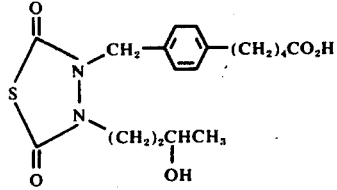 | " |

[a]Footnote a, Table I also applies to Table II.

Prostaglandin-like compounds are well recognized for their pharmacological value, e.g., as nasal decongestants, bronchodilators, abortifacients, labor inducers, antihypertensives, etc.

The 3,4-disubstituted-1,3,4-thiadiazoline-2,5-diones of this invention are prostaglandin mimics (or agonists), that is they have biological properties that simulate those of some of the natural prostaglandins; or are prostaglandin inhibitors, that is they inhibit biological responses normally brought about by prostaglandins. Whether a given compound acts as a prostaglandin mimic or inhibitor can depend on the dose level and the biological system involved. As prostaglandin mimics or inhibitors the compounds of this invention are useful for the study, prevention, amelioration, or cure of a variety of conditions or disorders that involve natural prostaglandins in man or in animals.

Stimulation of certain in vitro smooth muscle preparations is commonly taken as a measure of prostaglandin-like activity. Rat stomach (fundus) and uterus are two muscles that are conventional indicators of such activity. Table III lists for two of the 3,4-disubstituted-1,3,4-thiadiazoline-2,5-diones of this invention the concentrations in $\mu$g/ml required to induce contractions in these two kinds of smooth muscle with an intensity equivalent to that produced by 4 ng/ml of the natural prostaglandin $E_1$.

The smooth muscle stimulation by prostaglandins is discussed by Horton, Brit. Journal Pharmacol., 24, 472 (1956) and J. E. Pike et al., in Prostaglandins, Nobel Symposium No. 2, S. Bergstrom and B. Samuelson, ed., Interscience, Stockholm, 1967, p. 161. The rat uterus assay (B. Berde and K. Saameli, "Evaluation of Substances Acting on the Uterus" in Methods in Drug Evaluation, P. Mentegazza and F. Piccinini, editors, North-Holland, Amsterdam, 1966) was done as follows. Female rats are sacrificed by decapitation, and the uterus is removed. Each horn of the uterus is suspended in a 20 ml bath in de Jalon's solution at pH 7.6 and 32° C. Test drugs are added as small aliquots of concentrated solution and mixing is accomplished by continuous bubbling of air through the bath. Responses of the muscle are monitored isometrically by means of a strain gauge force displacement transducer.

The rat stomach assay (J. R. Vane, Brit. J. Pharmacol., 12, 344 (1957)) was done as follows. Male rats are decapitated and a strip is cut from the fundus of the stomach along the greater curvature. The strip (3 to 5 mm wide, and 3 to 4 cm long) is suspended in Tyrode solution at pH 7.1 and 37° C, and gassed continuously with oxygen. Addition of test drugs and recording techniques are identical to those for the uterus.

The topical anti-inflammatory assay (G. Tonelli, I. Thibault, and I. Ringler, Endocrinology, 77, 625 (1965)) was done as follows. Croton oil was applied to one ear of a mouse as a 1% solution in 80% ethanol: 20% pyridine. Five hours later, the mice are sacrificed with chloroform and standard ⅝ inches discs are punched from each ear. The degree of inflammation is measured by subtracting the weight of the control disc from the weight of the disc from the treated ear. Test drugs are dissolved in the ethanol-pyridine-croton oil mixture for evaluation by the above procedure.

TABLE III 3,4-Disubstituted-1,3,4-thiadiazoline-2,5-diones as Prostaglandin Mimics

| | | Mimic Activity, $\mu$gml$^{-1}$ vs 4 ngml$^{-1}$ of $PGE_1$ | |
|---|---|---|---|
| Example | Structure | Rat Uterus | Rat Stomach |
| 2. | 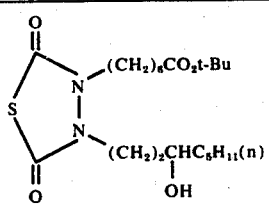 | 2 | (Antagonist) |

TABLE III-continued
3,4-Disubstituted-1,3,4-thiadiazoline-2,5-diones as Prostaglandin Mimics

| Example | Structure | Mimic Activity, $\mu gml^{-1}$ vs 4 $ngml^{-1}$ of $PGE_1$ | |
|---|---|---|---|
| | | Rat Uterus | Rat Stomach |
| 6. | S–C(=O)–N((CH$_2$)$_6$CO$_2$H)–N((CH$_2$)$_2$CHC$_5$H$_{11}$(n)OH)–C(=O) | (Antagonist) | 1 |

As prostaglandin mimics, the compounds can be expected to inhibit the secretion of gastric acid and thus find use for the study or treatment of gastric ulcers. Also, having a prostaglandin-like effect on uterine tissue, they are expected to cause abortion or induction of labor, e.g., in farm animals. As mimics of prostaglandin $E_1$, these compounds also are expected to cause bronchodilation.

Table IV lists for several of the compounds of this invention, the concentrations in $\mu g/ml$ required to inhibit the contraction of rat uterus strips (smooth muscle) caused by 100 ng/ml of the natural prostaglandin $E_1$.

TABLE IV
3,4-Disubstituted-1,3,4-thiadiazoline-2,5-diones as Prostaglandin Antagonists

| Example | Structure | Antagonist Activity, $\mu gml^{-1}$ vs 100 $ngml^{-1}$ of $PGE_1$, rat uterus |
|---|---|---|
| 2. | S–C(=O)–N((CH$_2$)$_6$CO$_2$t-Bu)–N((CH$_2$)$_2$CHC$_5$H$_{11}$(n)OH)–C(=O) | 20 |
| 1. | S–C(=O)–N((CH$_2$)$_6$CO$_2$Et)–N((CH$_2$)$_2$CHC$_5$H$_{11}$(n)OH)–C(=O) | 20 |
| 6. | S–C(=O)–N((CH$_2$)$_6$CO$_2$H)–N((CH$_2$)$_2$CHC$_5$H$_{11}$(n)OH)–C(=O) | 40 |

Under some conditions some of the compounds of this invention also have biological properties opposite to those of the natural prostaglandins. Prostaglandin $E_1$ causes inflammation when applied directly to skin. Non-steroidal antiinflammatory agents are known to inhibit the in vivo synthesis of prostaglandins which are known to be among the natural mediators of inflammation, and at least some steroid antiinflammatory agents have been found to inhibit the cellular release of prostaglandins. The ethyl ester 6 (Ex. 1) and acid 8 (Ex. 6) afford some protection from the inflammatory effects induced in mouse ears by topically applied croton oil irritant.

The metal salts and amine salts of the carboxylic acids have biological properties similar to those of the corresponding acids.

The compounds of the invention can be employed in pharmaceutical compositions comprising one or more compounds of the invention and a non-toxic pharmaceutical carrier, and if desired, with various additives, etc. as is known in the art. Pharmaceutical compositions include injectables, tablets, gelatin capsules, suspensions, syrups, elixirs and the like. Additives include solvents, diluents, lubricating agents, binders, disintegrants, preservatives, colorants and flavors, etc. all as is known in the art. The compositions can be administered to humans and animals by any of the known routes, e.g., nasal, oral, parenteral, anal or topical application. The compounds can also be formulated in polymeric matrices for sustained release. Particularly useful are biodegradable polymer matrices, such as homopolymers of lactic acid or glycolic acid, mixtures thereof, or their copolymers. These drug-polymer compositions can be injected as small particles in suspension, implanted as pellets, or sprayed on skin or lesions as films. The active component is then released slowly and the polymer is degraded to physiologically normal substances.

I claim:
1. A compound having the formula

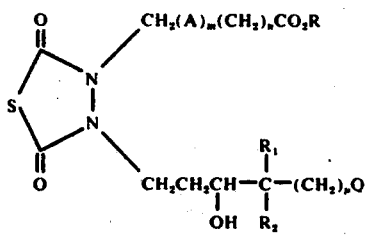

in which
A is CH=CH, CH, C≡C or phenylene;
$R_4, R_5$ and $R_6$ does not exceed 10;
m is 0 or 1;
$R_3$ is H,
$R_4$, $R_5$ and $R_6$ individually are H, alkyl of 1-4 carbons or hydroxyalkyl of 2-4 carbons with the proviso that the total number of carbon atoms in $R_4$, $R_5$ and $R_6$ does not exceed 10; p1
m is 0 or 1; n is 2 to 6;
p is 90 to 6;
$R_1$ and $R_2$ individually are H, F or $CH_3$; and
Q is H, $CH_3$, $CF_2CH_3$ or $CF_3$.

2. A compound of claim 1 where A is cis CH=CH, C≡C or p-phenylene.

3. A compound of claim 1 where A is CH=CH or C≡C and the chain length of $-CH_2(A)_m(CH_2)_n CO_2-$ is 7 carbons.

4. A compound of claim 1 where m=0 and n=5.
5. A compound of claim 1 wherein m=1 and n=2 or 3.
6. A compound of claim 1 where p=3 or 5.
7. A compound of claim 1 where Q=H, $CH_3$ or $CF_3$.
8. A compound of claim 1 wherein R=H.
9. A compound of claim 1 wherein $R_1$ and $R_2$ are each H, F or $CH_3$.
10. A compound of claim 1 which is 4-(3-hydroxyoctyl)-2,5-dioxo-1,3,4-thiadiazoline-3-heptanoic acid.
11. The ethyl ester of the compound of claim 10.
12. The tertiary butyl ester of the compound of claim 10.
13. A compound of the formula

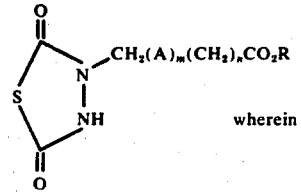

wherein wherein
A is CH=CH, C≡C or phenylene;
m is 0 or 1;
n is 2 to 6; and
R is H, alkali metal, alkyl or cycloalkyl of up to 10 carbons, $NHC(CH_2OH)_3$ or $NR_3R_4R_5R_6$ in which $R_3$ is H;
$R_4$, $R_5$ and $R_6$ individually are H, alkyl of 1-4 carbons, or hydroxyalkyl of 2-4 carbons with the proviso that the total number of carbon atoms in $R_4$, $R_5$ and $R_6$ does not exeed 10.
14. A compound of claim 13 in which R is alkyl.
15. A compound of claim 13 in which R is t-butyl.
16. A compound of claim 13 in which R is ethyl.

* * * * *

UNITED STATES PATENT OFFICE
CERTIFICATE OF CORRECTION

PATENT NO. : 4,032,533
DATED : June 28, 1977
INVENTOR(S) : Richard Merrill Scribner It is certified that error appears in the above-identified patent and that said Letters Patent are hereby corrected as shown below:

Column 1, line 68, "p-$C_{64}$" should be --p-$C_6H_4$--.

Column 2, line 8, "C C" should be --C≡C--.

Column 49, line 21, "A is CH=CH, CH, C≡C" should be --A is CH=CH, C≡C--.

Column 49, lines 22 and 23, "$R_4$, $R_5$ and $R_6$ does not exceed 10; m is 0 or 1;" should be --R is H, alkali metal, alkyl or cycloalkyl of up to 10 carbons, $NHC(CH_2OH)_3$ or $NR_3R_4R_5R_6$ in which--.

Column 49, line 29, "not exceed 10; pl" should be --not exceed 10;--.

Column 49, line 31, "p is 90 to 6;" should be --p is 0 to 6;--.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks